US008423531B2

(12) United States Patent
Yamakawa et al.

(10) Patent No.: US 8,423,531 B2
(45) Date of Patent: Apr. 16, 2013

(54) NON-TRANSITORY STORAGE MEDIUM STORING MANAGEMENT PROGRAM, MANAGEMENT APPARATUS, AND MANAGEMENT METHOD

(75) Inventors: Kazuo Yamakawa, Takamatsu (JP); Isao Sumito, Takamatsu (JP); Kazuma Takahashi, Takamatsu (JP); Kenji Sakata, Kawasaki (JP); Hitoshi Kamura, Takamatsu (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/043,237

(22) Filed: Mar. 8, 2011

(65) Prior Publication Data

US 2011/0225187 A1  Sep. 15, 2011

(30) Foreign Application Priority Data

Mar. 11, 2010  (JP) .................................. 2010-54070

(51) Int. Cl.
G06F 7/00 (2006.01)
G06F 17/30 (2006.01)

(52) U.S. Cl.
USPC ........................... 707/707; 707/796; 600/300

(58) Field of Classification Search .................. 707/707, 707/E17.014, 796; 600/300
See application file for complete search history.

(56) References Cited

U.S. PATENT DOCUMENTS

| 5,471,382 A * | 11/1995 | Tallman et al. ............... 600/300 |
| 5,764,923 A * | 6/1998 | Tallman et al. ................... 705/3 |
| 5,868,669 A * | 2/1999 | Iliff ............................. 600/300 |
| 6,071,236 A * | 6/2000 | Iliff ............................. 600/300 |
| 6,256,614 B1 * | 7/2001 | Wecker et al. ............. 705/14.19 |
| 2002/0038227 A1 * | 3/2002 | Fey et al. .......................... 705/3 |
| 2003/0163488 A1 * | 8/2003 | Kloos et al. .................... 707/200 |
| 2004/0129769 A1 * | 7/2004 | Kovach ......................... 235/375 |
| 2004/0153456 A1 * | 8/2004 | Charnock et al. ............... 707/10 |
| 2004/0249778 A1 * | 12/2004 | Iliff ................................. 706/45 |
| 2005/0010451 A1 * | 1/2005 | Marks et al. ...................... 705/3 |

(Continued)

FOREIGN PATENT DOCUMENTS

JP  2004-220599  8/2004

OTHER PUBLICATIONS

Takumi Ishida and Katsunori Kurusu—"Clinical trial procedures and approval processes in Japan"—Targeted Regulatory Writing Techniques. Clinical Documents for Drugs and Biologics—edited by Linda Fossati Wood and MaryAnn Foote—2009 Birkhäuser Verlag Basel/Switzerland—Part 5, (pp. 155-174).*

(Continued)

Primary Examiner — Anh Ly
(74) Attorney, Agent, or Firm — Fujitsu Patent Center

(57) ABSTRACT

A non-transitory storage medium storing a management program, the management program causing a computer to execute first receiving case data related to a result of a clinical trial; referring to a definition table storing a first criterion and a second criterion; determining whether or not the case data satisfies the first criterion or second criterion; first transmitting a first inquiry to a terminal; second transmitting a second inquiry to the terminal; second receiving a first answer to the first inquiry from the terminal, the first answer including other case data that is the case data at least a part of which is modified; third determining whether or not the other case data satisfies the second criterion; and making a second answer to the second inquiry on the basis of a result of the third determination.

24 Claims, 21 Drawing Sheets

U.S. PATENT DOCUMENTS

| | | | | |
|---|---|---|---|---|
| 2006/0282222 A1* | 12/2006 | Mitsuyama et al. | 702/19 |
| 2007/0271830 A1* | 11/2007 | Holt et al. | 42/70.01 |
| 2007/0276694 A1* | 11/2007 | Moriyama | 705/2 |
| 2008/0033658 A1* | 2/2008 | Dalton et al. | 702/19 |
| 2008/0303638 A1* | 12/2008 | Nguyen et al. | 340/10.42 |
| 2009/0043449 A1* | 2/2009 | Matsuura et al. | 701/36 |
| 2009/0209646 A1* | 8/2009 | Moore et al. | 514/561 |
| 2009/0260577 A1* | 10/2009 | Lewis, II | 119/165 |
| 2011/0225187 A1* | 9/2011 | Yamakawa et al. | 707/770 |

OTHER PUBLICATIONS

Adnan I. Qureshi—"Taking a Closer Look at Trials—Antihypertensive Treatment of Acute Cerebral Hemorrhage (ATACH)"—Rationale and Design—Neurocritical Care Copyright © 2007 Humana Press Inc. ISSN 1541-6933/07/6:56-66 ISSN 1556-0961 (Online) DOI: 10.1385/Neurocrit. Care Jun. 2007, (pp. 56-66).*

* cited by examiner

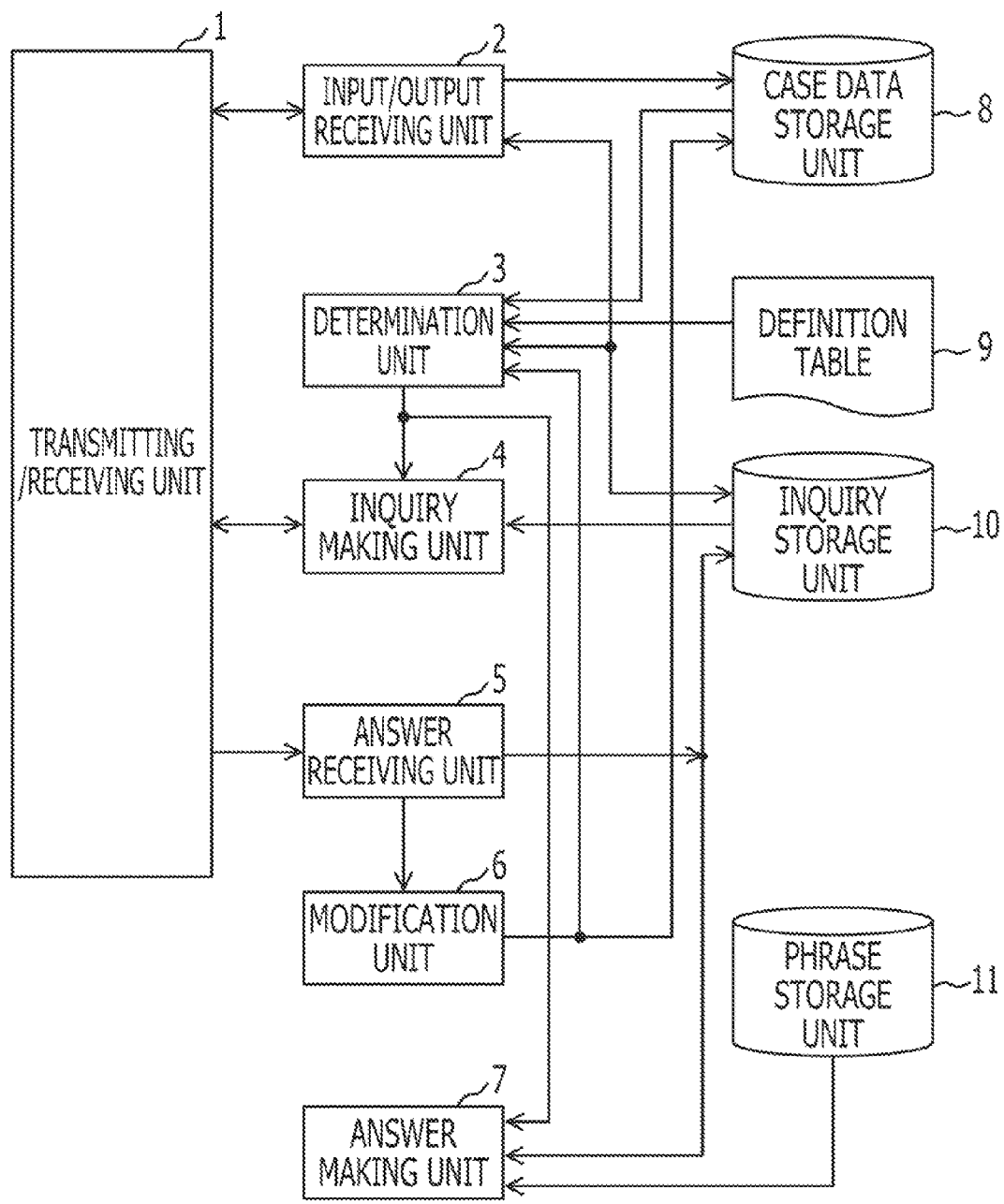

FIG. 11

| CATEGORY | ITEM | | CASE DATA | | |
|---|---|---|---|---|---|
| HUMAN SUBJECT INFORMATION | HUMAN SUBJECT ID | | h-0001 | h-0002 | ... |
| | CASE NUMBER | | s0001-001 | s0001-002 | ... |
| | DISORDER | | HIGH BLOOD PRESSURE | STROKE | ... |
| | BIRTH DATE | | 1953.5.10 | 1943.12.20 | ... |
| | AGE | | 56 | 66 | ... |
| | SEX | | MALE | FEMALE | ... |
| | BODY HEIGHT (cm) | | 160 | 150 | ... |
| | BODY WEIGHT (kg) | | 60 | 50 | ... |
| | ... | | ... | ... | ... |
| INFORMATION OF CLINICAL TRIAL FACILITY | NAME OF CLINICAL TRIAL EXECUTION FACILITY | | TOKYO HOSPITAL | KYOTO HOSPITAL | ... |
| | NAME OF PHYSICIAN-IN-CHARGE | | TOKYO TARO | KYOTO JIRO | ... |
| | ... | | ... | ... | ... |
| CLINICAL TRIAL CONTENT | METHOD OF CLINICAL TRIAL | | MEDICATION | MEDICATION | ... |
| | CLINICAL TRIAL START DATE | | 2009.11.10 | 2009.12.10 | ... |
| | ... | | ... | ... | ... |
| DRUG | NAME OF USED DRUG | | DRUG A | DRUG B | ... |
| | DRUG ADMINISTRATION DATE | | 2009.11.10 | 2009.12.15 | ... |
| | DRUG-TAKING CONDITION | | AFTER EACH MEAL | AFTER EACH MEAL | ... |
| | ... | | ... | ... | ... |
| DIAGNOSTIC INTERVIEW/TEST | DATE OF DIAGNOSTIC INTERVIEW (VISIT) | | 2009.11.15 | 2009.12.20 | ... |
| | RESULT OF DIAGNOSTIC INTERVIEW | SYSTOLIC BLOOD PRESSURE (mmHg) | 100 | 150 | ... |
| | | DIASTOLIC BLOOD PRESSURE (mmHg) | 100 | 85 | ... |
| | | ... | ... | ... | ... |
| | DATE OF TEST REQUEST TO TEST FACILITY | | - | 2009.12.20 | ... |
| | SAMPLE COLLECTION DATE | | - | 2009.12.20 | ... |
| | TEST CONTENT | | - | BLOOD TEST | ... |
| | TEST RESULT | THE NUMBER OF RED BLOOD CELLS (/mm3) | - | 5,000,000 | ... |
| | | THE NUMBER OF WHITE BLOOD CELLS (/mm3) | - | 2000 | ... |
| | | ... | ... | ... | ... |
| | ... | | ... | ... | ... |
| TEST FACILITY INFORMATION | NAME OF TEST EXECUTION FACILITY | | - | TEST COMPANY A | ... |
| | TEST EXECUTION DATE | | - | 2009.12.21 | ... |
| | ... | | ... | ... | ... |

FIG. 12

| | Item Name | Data Type | The Number of Digits | Allowed Value Range | Relationship Between Items |
|---|---|---|---|---|---|
| HUMAN SUBJECT INFORMATION | HUMAN SUBJECT ID | ALPHANUMERIC CHARACTERS | 10 | · | · |
| | CASE NUMBER | ALPHANUMERIC CHARACTERS | 10 | · | · |
| | DISORDER | TEXT | · | · | · |
| | BIRTH DATE | DATE | · | · | · |
| | AGE | NUMERICAL VALUE | 3 | 0 - 150 | · |
| | SEX | TEXT | · | · | · |
| | BODY HEIGHT (cm) | NUMERICAL VALUE | 3 | 0 - 200 | · |
| | BODY WEIGHT (kg) | NUMERICAL VALUE | 3 | 3 - 150 | · |
| | ... | ... | ... | ... | ... |
| INFORMATION OF CLINICAL TRIAL FACILITY | NAME OF CLINICAL TRIAL EXECUTION FACILITY | TEXT | · | · | · |
| | ... | ... | ... | ... | ... |
| DIAGNOSTIC INTERVIEW/TEST | DATE OF DIAGNOSTIC INTERVIEW (VISIT) | DATE | · | · | · |
| | RESULT OF DIAGNOSTIC INTERVIEW — SYSTOLIC BLOOD PRESSURE (mmHg) | NUMERICAL VALUE | 3 | 110 - 180 | SYSTOLIC BLOOD PRESSURE > DIASTOLIC BLOOD PRESSURE |
| | RESULT OF DIAGNOSTIC INTERVIEW — DIASTOLIC BLOOD PRESSURE (mmHg) | NUMERICAL VALUE | 3 | 50 - 100 | SYSTOLIC BLOOD PRESSURE > DIASTOLIC BLOOD PRESSURE |
| | ... | ... | ... | ... | ... |
| | DATE OF TEST REQUEST TO TEST FACILITY | DATE | · | · | · |
| | SAMPLE COLLECTION DATE | DATE | · | · | · |
| | TEST CONTENT | TEXT | · | · | · |
| | TEST RESULT — THE NUMBER OF RED BLOOD CELLS (/mm³) | NUMERICAL VALUE | 8 | 380 - 5,400,000 | · |
| | TEST RESULT — THE NUMBER OF WHITE BLOOD CELLS (/mm³) | NUMERICAL VALUE | 5 | 4000 - 8000 | · |
| | ... | ... | ... | ... | ... |

FIG. 13

| | QRY-0001 | QRY-0002 | QRY-0003 | QRY-0004 | ... |
|---|---|---|---|---|---|
| INQUIRY ID | QRY-0001 | QRY-0002 | QRY-0003 | QRY-0004 | ... |
| HUMAN SUBJECT ID | h-0001 | h-0001 | h-0002 | h-0003 | ... |
| CASE NUMBER | S0001-001 | S0001-001 | S0002-002 | S0003-003 | ... |
| DATE OF DIAGNOSTIC INTERVIEW (VISIT) | 2009.11.15 | 2009.11.15 | 2009.11.20 | 2009.11.21 | ... |
| NAME OF CLINICAL TRIAL EXECUTION FACILITY | TOKYO HOSPITAL | TOKYO HOSPITAL | KYOTO HOSPITAL | OSAKA HOSPITAL | ... |
| TYPE OF INQUIRY | AUTOMATIC | AUTOMATIC | AUTOMATIC | MANUAL | ... |
| CONTENT OF INQUIRY | THE SYSTOLIC BLOOD PRESSURE IS THE SAME AS THE DIASTOLIC BLOOD PRESSURE. PLEASE CHECK AGAIN. | RANGE ERROR | RANGE ERROR | THE BODY HEIGHT IS 143 cm, ISN'T IT? | ... |
| INQUIRY ITEM — ITEM CONTENT (1) | SYSTOLIC BLOOD PRESSURE \| 100 | SYSTOLIC BLOOD PRESSURE \| 100 | THE NUMBER OF WHITE BLOOD CELLS \| 2000 | BODY HEIGHT \| 143 | ... |
| INQUIRY ITEM — ITEM CONTENT (2) | DIASTOLIC BLOOD PRESSURE \| 100 | - | - | - | ... |
| INQUIRY ITEM — ... | ... | ... | ... | ... | ... |
| CRF | BLOOD PRESSURE MEASUREMENT | BLOOD PRESSURE MEASUREMENT | BLOOD PRESSURE MEASUREMENT | BODY MEASUREMENT | ... |
| STATE OF INQUIRY | ISSUED | ISSUED | ISSUED | ISSUED | ... |
| ERROR ATTRIBUTE | RELATIONSHIP BETWEEN ITEMS | ALLOWED VALUE RANGE | ALLOWED VALUE RANGE | - | ... |
| ... | ... | ... | ... | ... | ... |

SEARCH SCREEN
· HUMAN SUBJECT NUMBER
· CASE NUMBER
· NAME OF CLINICAL TRIAL EXECUTION FACILITY
· TYPE OF INQUIRY
· INQUIRY ID

☑ AUTOMATIC INQUIRY    ☑ MANUAL INQUIRY

20

SEARCH — 21

INQUIRY LIST
1 2 3 4

| INQUIRY ID | NAME OF CLINICAL TRIAL EXECUTION FACILITY | HUMAN SUBJECT NUMBER | CASE NUMBER | TYPE OF INQUIRY | CONTENT OF INQUIRY |
|---|---|---|---|---|---|
| QRY-0001 | TOKYO HOSPITAL | h-0001 | S0001-001 | AUTOMATIC | THE SYSTOLIC BLOOD PRESSURE IS THE SAME AS THE DIASTOLIC BLOOD PRESSURE. PLEASE CHECK AGAIN. |
| QRY-0002 | TOKYO HOSPITAL | h-0001 | S0001-001 | AUTOMATIC | RANGE ERROR |
| QRY-0003 | KYOTO HOSPITAL | h-0002 | S0002-002 | AUTOMATIC | RANGE ERROR |
| ... | ... | ... | ... | ... | ... |

ANSWER SCREEN

◆ INQUIRY DETAILS

- INQUIRY ID: QRY-0001
- TYPE OF INQUIRY: AUTOMATIC
- CONTENT OF INQUIRY: THE SYSTOLIC BLOOD PRESSURE IS THE SAME AS THE DIASTOLIC BLOOD PRESSURE. PLEASE CHECK AGAIN.

- ISSUER: FUJITSU JIRO
- HUMAN SUBJECT NUMBER: h-0001
- DATE OF DIAGNOSTIC INTERVIEW (VISIT): 2009.11.15

- DATE AND TIME OF ISSUE: 2009.11.16,11:12:12
- CASE NUMBER: S0001-001
- CRF: BLOOD PRESSURE MEASUREMENT

◆ ANSWER FIELD

ANSWER INPUT

| INQUIRY ITEM | BEFORE MODIFICATION | MODIFICATION | NON-MEASUREMENT | AFTER MODIFICATION | REASON FOR THE MODIFICATION |
|---|---|---|---|---|---|
| SYSTOLIC BLOOD PRESSURE | 100 | ☐ | ☐ | | |
| DIASTOLIC BLOOD PRESSURE | 100 | ☐ | ☐ | | |

ANSWER

FIG. 16

ANSWER SCREEN

◆ INQUIRY DETAILS — 24

- INQUIRY ID: QRY-0001
- TYPE OF INQUIRY: AUTOMATIC
- CONTENT OF INQUIRY: THE SYSTOLIC BLOOD PRESSURE IS THE SAME AS THE DIASTOLIC BLOOD PRESSURE. PLEASE CHECK AGAIN.

- ISSUER: FUJITSU JIRO
- HUMAN SUBJECT NUMBER: h-0001
- DATE OF DIAGNOSTIC INTERVIEW (VISIT): 2009.11.15

- DATE AND TIME OF ISSUE: 2009.11.16 11:12:12
- CASE NUMBER: S0001-01
- CRF: BLOOD PRESSURE MEASUREMENT

◆ ANSWER FIELD — 25

ANSWER INPUT: MODIFY THE SYSTOLIC BLOOD PRESSURE — 26

| INQUIRY ITEM | BEFORE MODIFICATION | MODIFICATION | NON-MEASUREMENT | AFTER MODIFICATION | REASON FOR THE MODIFICATION |
|---|---|---|---|---|---|
| SYSTOLIC BLOOD PRESSURE | 100 | ☑ | ☐ | 150 | INPUT ERROR |
| DIASTOLIC BLOOD PRESSURE | 100 | ☐ | ☐ | | |

— 27

[ANSWER] — 28

FIG. 17

| | QRY-0001 | QRY-0002 | QRY-0003 | QRY-0004 | ... |
|---|---|---|---|---|---|
| INQUIRY ID | | | | | |
| HUMAN SUBJECT ID | h-0001 | h-0001 | h-0002 | h-0003 | ... |
| CASE NUMBER | S0001-001 | S0001-001 | S0002-002 | S0003-003 | ... |
| DATE OF DIAGNOSTIC INTERVIEW (VISIT) | 2009.11.15 | 2009.11.15 | 2009.11.20 | 2009.11.21 | ... |
| NAME OF CLINICAL TRIAL EXECUTION FACILITY | TOKYO HOSPITAL | TOKYO HOSPITAL | KYOTO HOSPITAL | OSAKA HOSPITAL | ... |
| TYPE OF INQUIRY | AUTOMATIC | AUTOMATIC | AUTOMATIC | MANUAL | ... |
| CONTENT OF INQUIRY | THE SYSTOLIC BLOOD PRESSURE IS THE SAME AS THE DIASTOLIC BLOOD PRESSURE. PLEASE CHECK AGAIN. | RANGE ERROR | RANGE ERROR | THE BODY HEIGHT IS 143 cm, ISN'T IT? | ... |
| INQUIRY ITEM — ITEM CONTENT (1) | SYSTOLIC BLOOD PRESSURE 100 | SYSTOLIC BLOOD PRESSURE 100 | THE NUMBER OF WHITE BLOOD CELLS 2000 | BODY HEIGHT 143 | ... |
| INQUIRY ITEM — ITEM CONTENT (2) | DIASTOLIC BLOOD PRESSURE 100 | - | - | - | ... |
| CRF | BLOOD PRESSURE MEASUREMENT | BLOOD PRESSURE MEASUREMENT | BLOOD PRESSURE MEASUREMENT | BODY MEASUREMENT | ... |
| STATE OF INQUIRY | CLOSE | ISSUED | ISSUED | ISSUED | ... |
| ERROR ATTRIBUTE | RELATIONSHIP BETWEEN ITEMS | ALLOWED VALUE RANGE | ALLOWED VALUE RANGE | - | ... |
| ANSWER INPUT | MODIFY THE SYSTOLIC BLOOD PRESSURE | - | - | - | ... |
| MODIFIED ITEM (1) | SYSTOLIC BLOOD PRESSURE 150 | - | - | - | ... |
| REASON FOR MODIFICATION | INPUT ERROR | - | - | - | ... |

FIG. 18

| PHRASE ID | PHRASE |
|---|---|
| K0001 | IN THE INQUIRY ID [ID NUMBER], [ITEM] IS MODIFIED FROM [VALUE BEFORE MODIFICATION] TO [VALUE AFTER MODIFICATION] DUE TO [REASON FOR THE MODIFICATION], AND THUS THE CONDITION OF THE INQUIRY (INQUIRY ID [ID NUMBER]) IS SATISFIED, SO THAT THE INQUIRY IS AUTOMATICALLY CLOSED. |
| K0002 | THE CAUSE OF THE INQUIRY IS SOLVED DUE TO AN ERROR OF ITEM FIELD WHERE CASE DATA SHOULD BE INPUTTED, SO THAT THE INQUIRY IS AUTOMATICALLY CLOSED. |
| ⋮ | ⋮ |

FIG. 19

| | | | | |
|---|---|---|---|---|
| INQUIRY ID | QRY-0001 | QRY-0002 | QRY-0003 | QRY-0004 |
| HUMAN SUBJECT ID | h-0001 | h-0001 | h-002 | h-0003 |
| CASE NUMBER | S0001-001 | S0001-001 | S0002-002 | S0003-003 |
| DATE OF DIAGNOSTIC INTERVIEW (VISIT) | 2009.11.15 | 2009.11.15 | 2009.11.20 | 2009.11.21 |
| NAME OF CLINICAL TRIAL EXECUTION FACILITY | TOKYO HOSPITAL | TOKYO HOSPITAL | KYOTO HOSPITAL | OSAKA HOSPITAL |
| TYPE OF INQUIRY | AUTOMATIC | AUTOMATIC | AUTOMATIC | MANUAL |
| CONTENT OF INQUIRY | THE SYSTOLIC BLOOD PRESSURE IS THE SAME AS THE DIASTOLIC BLOOD PRESSURE. PLEASE CHECK AGAIN. | | RANGE ERROR | THE BODY HEIGHT IS 143 cm, ISN'T IT? |
| INQUIRY ITEM / ITEM CONTENT (1) | SYSTOLIC BLOOD PRESSURE 100 | SYSTOLIC BLOOD PRESSURE 10 | THE NUMBER OF WHITE BLOOD CELLS 2400 | BODY HEIGHT 143 |
| ITEM CONTENT (2) | DIASTOLIC BLOOD PRESSURE 100 | | | |
| CRF | BLOOD PRESSURE MEASUREMENT | BLOOD PRESSURE MEASUREMENT | BLOOD PRESSURE MEASUREMENT | BODY MEASUREMENT |
| STATE OF INQUIRY | CLOSE | ISSUED | ISSUED | ISSUED |
| ERROR ATTRIBUTE | RELATIONSHIP BETWEEN ITEMS | ALLOWED VALUE RANGE | ALLOWED VALUE RANGE | |
| ANSWER INPUT | MODIFY THE SYSTOLIC BLOOD PRESSURE | IN THE INQUIRY ID "QRY-0001", "SYSTOLIC BLOOD PRESSURE IS MODIFIED FROM "100" TO "130" DUE TO "INPUT ERROR", AND THUS THE CONDITION OF THE INQUIRY (INQUIRY ID "QRY-0002") IS SATISFIED, SO THAT THE INQUIRY IS AUTOMATICALLY CLOSED. | | |
| MODIFIED ITEM (1) | SYSTOLIC BLOOD PRESSURE 130 | | | |
| REASON FOR MODIFICATION | INPUT ERROR | | | |

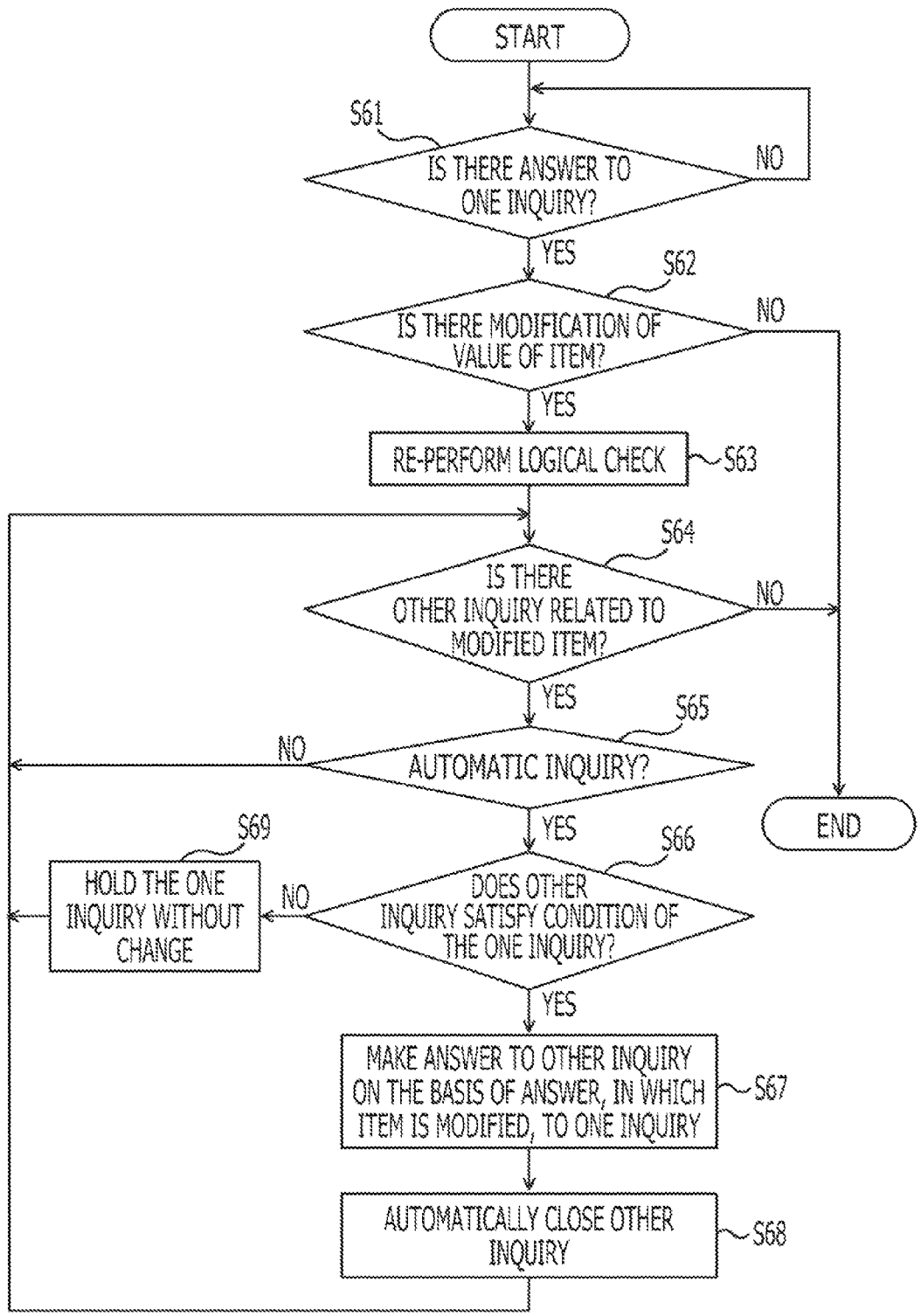

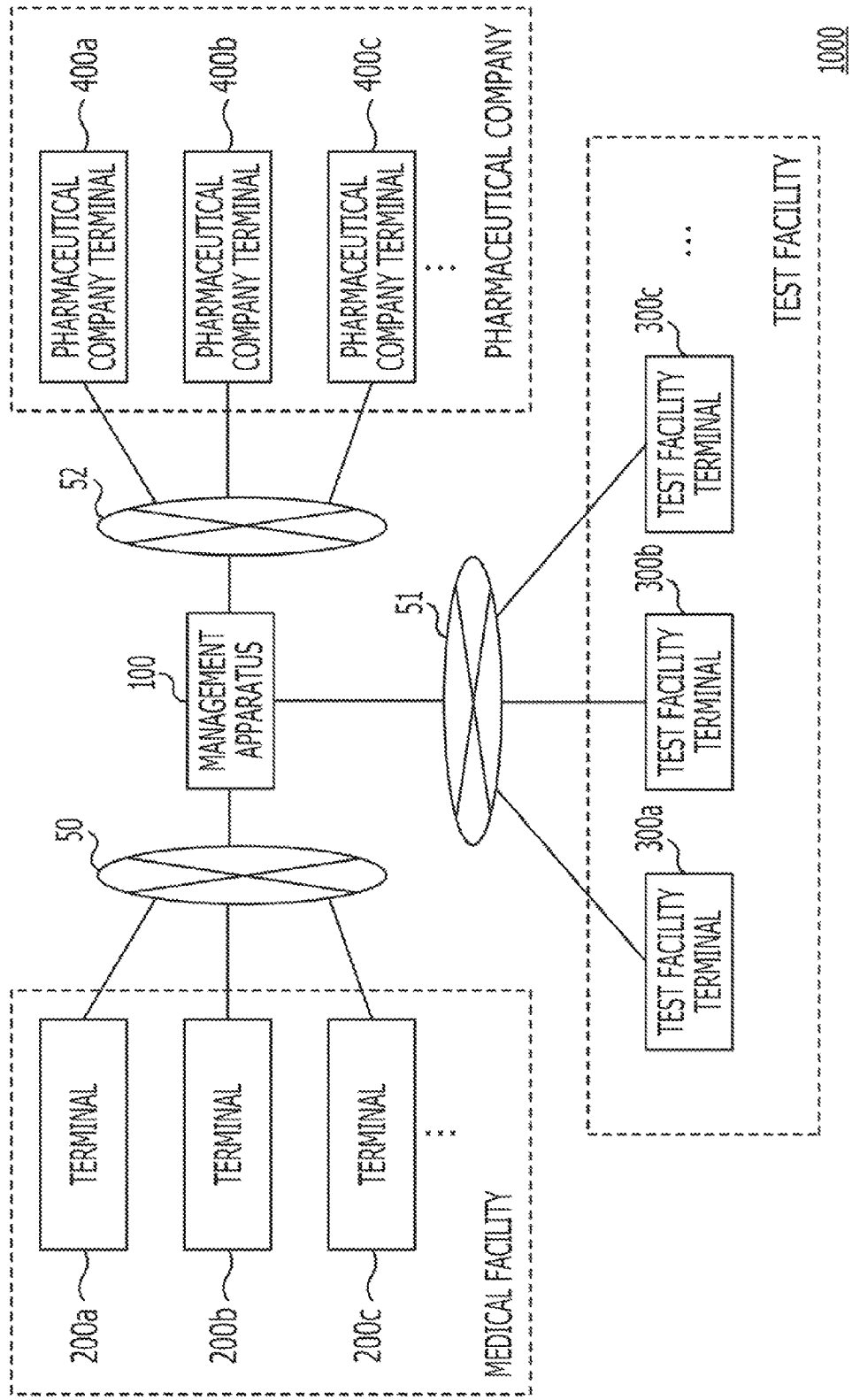

NON-TRANSITORY STORAGE MEDIUM STORING MANAGEMENT PROGRAM, MANAGEMENT APPARATUS, AND MANAGEMENT METHOD

CROSS-REFERENCE TO RELATED APPLICATIONS

This application is based upon and claims the benefit of priority of the prior Japanese Patent Application No. 2010-54070, filed on Mar. 11, 2010, the entire contents of which are incorporated herein by reference.

FIELD

An embodiment relates to a technique for managing case data.

BACKGROUND

When a pharmaceutical company develops a new drug, the new drug is administered to animals and the drug efficacy is evaluated. Further, clinical investigation, or so-called clinical trial, in which the new drug is administered to human beings, is performed. The pharmaceutical company submits a result of the clinical trial to the U.S. Food and Drug Administration. When the new drug has passed the approval process, the pharmaceutical company can sell the new drug in the open market. In the clinical trial, first, the pharmaceutical company requests a medical facility to perform the clinical trial. A physician-in-charge of the medical facility observes the health status of a human subject through diagnostic interview before and after administering the new drug to the human subject. In addition, the physician-in-charge collects samples such as blood and urine from the human subject before and after administering the new drug to the human subject. A test facility tests the collected samples and reports the test result to the medical facility. Among the pharmaceutical company, the medical facility, and the test company, various case data related to the clinical trial are transmitted and received, and the case data is recorded on the case report form (CRF). A system in which the case report form is computerized and managed is disclosed in Japanese Patent Application Publication No. 2004-220599.

SUMMARY

According to an aspect of the invention, a non-transitory storage medium storing a management program, the management program causing a computer to execute first receiving case data related to a result of a clinical trial; referring to a definition table storing a first criterion and a second criterion; first determining whether or not the case data satisfies the first criterion; first transmitting a first inquiry to a terminal when the case data does not satisfy the first criterion; second determining whether or not the case data satisfies the second criterion stored in the definition table; second transmitting a second inquiry to the terminal when the case data does not satisfy the second criterion; second receiving a first answer to the first inquiry from the terminal, the first answer including other case data that is the case data at least a part of which is modified; third determining whether or not the other case data satisfies the second criterion; and making a second answer to the second inquiry on the basis of a result of the third determination.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 10 is an example of a functional block diagram of the management apparatus according to an example;

FIG. 11 is an example of case data stored in a case data storage unit.

FIG. 12 is an example of a definition table;

FIG. 13 is an example of inquiries stored in an inquiry storage unit;

FIG. 14 is an example of a search screen;

FIG. 15 is an example of an answer screen;

FIG. 16 is an example of an answer inputted in the answer screen;

FIG. 17 is an example of the inquiry storage unit in which the answer is stored;

FIG. 18 is an example of a fixed phrase storage unit;

FIG. 19 is an example of the inquiry storage unit in which an answer to an automatic inquiry "QRY-0002" is stored;

FIG. 20 is a flowchart showing an example of processing performed by the management apparatus according to the example; and FIG. 21 is an example of a network configuration diagram of a management system according to another example.

DESCRIPTION OF EMBODIMENTS

The system disclosed in Japanese Patent Application Publication No. 2004-220599 can perform inspection of input omission in the case report form, the number of digits and an appropriate range of case data, and the like. If a problem is found in the inspection, the system issues an inquiry. Then, a user of the system, for example, a physician-in-charge answers the inquiry. The case report form is made for each human subject and for each cranial trial, and many items of case data are inputted in the case report form. The more the number of times of the diagnostic interviews and the more the number of test times of the samples in the clinical trial are, the more the number of the case data is. As a result, the number of inquiry issuances increases. It takes a great deal of effort for a user to answer the inquiries issued in a large quantity. As a result, it takes a long period of time to finish answering them.

The inventors propose a non-transitory storage medium storing a program capable of efficiently managing inquiries and answers related to inputted data, a management apparatus, and a management system.

(1) Peripheral Configuration of an Embodiment

A clinical trial of a new drug is performed by cooperation of a pharmaceutical company, a medical facility, and a test company. When a new drug is developed in the pharmaceutical company, a clinical trial protocol is created in accordance with the law and a clinical trial of the new drug is requested to the medical facility. In the medical facility which is requested to perform the clinical trial, a selected physician-in-charge performs the clinical trial by performing diagnostic interviews on human subjects and collecting samples such as blood and urine in accordance with the clinical trial protocol. The samples collected from the human subjects are tested in the test company, and the test result is reported to the medical facility.

Figure 1:
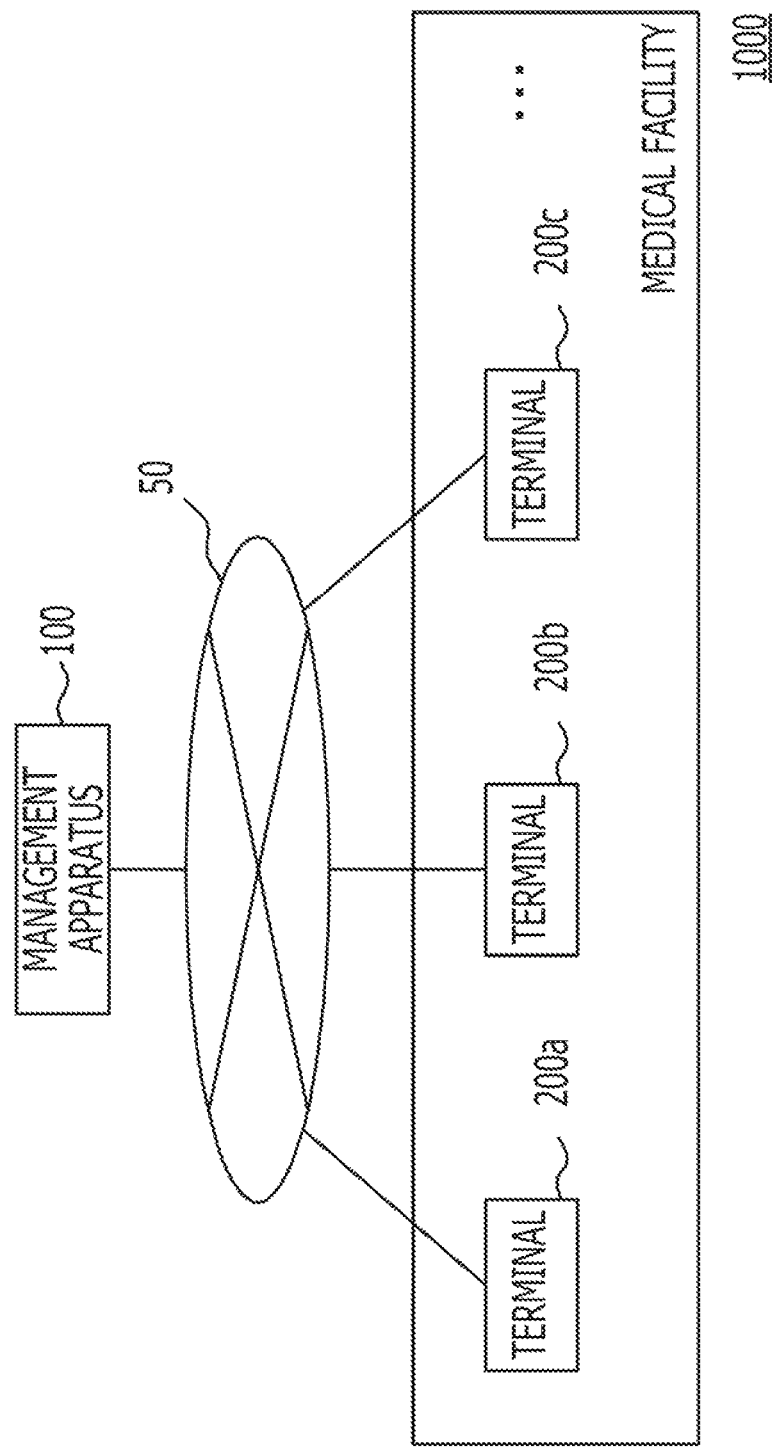
FIG. 1 is an example of a network configuration diagram of a management system according to an embodiment.

FIG. 1 is an example of a network configuration diagram of a management system according to an embodiment. A management system 1000 includes a management apparatus 100 and a terminal 200 installed in a medical facility. The management apparatus 100 and the terminal 200 are connected via a network 50. In addition, in a pharmaceutical company and a testing company, a pharmaceutical company terminal and a testing company terminal may be respectively installed and be able to access the management apparatus 100 via the network 50.

A physician-in-charge inputs case data such as a diagnostic interview result and a test result from the terminal 200 installed in the medical facility to make a case report form (CRF). The management apparatus 100 stores the inputted case data and manages the case data by performing a logical check described below.

The case report form includes a plurality of items, and case data is inputted into each item. Here, the items are sub-categories into which the case data is classified, and for example, there are items for identifying a human subject, such as a human subject number, and items for specifying condition of the human subject, such as a body height, a body weight, and a blood pressure of the human subject. The case data is a collective name of various data inputted into each item.

The management apparatus 100 checks whether or not the case data satisfies predetermined criteria for each item in the case report form. The check for determining whether or not the case data satisfies the predetermined criteria is referred to as a logical check. As the predetermined criteria, for example, there are criteria such as whether or not the inputted case data is incomplete, and whether or not the type of data, the number of digits, an allowed range, and the consistency in the case data are satisfied. When the management apparatus 100 determines that the case data does not satisfy the predetermined criteria in this logical check, the management apparatus 100 issues an inquiry. The inquiry is a warning indicating that the case data does not satisfy the predetermined criteria. When the management apparatus 100 transmits an inquiry to the terminal 200 in the medical facility, the physician-in-charge of the medical facility answers the inquiry.

(2) Overview of the Embodiment

In the embodiment, it is assumed that the management apparatus 100 issues a plurality of inquiries and receives an answer to one inquiry of the plurality of inquiries. At this time, if the answer to the one inquiry solves a cause by which another inquiry occurs, the management apparatus 100 makes an answer to the other inquiry on the basis of the answer to the one inquiry. Hereinafter, the cause by which another inquiry occurs is simply referred to as a cause of inquiry.

More specifically, when the management apparatus 100 receives an answer to one inquiry, the management apparatus 100 re-performs a logical check of the case data. As a result of the re-performed logical check, if a cause of another inquiry about the case data is solved, the management apparatus 100 makes an answer to the other inquiry on the basis of the answer to the one inquiry.

(2-1) About Inquiry and Close

The inquiries include automatic inquiries and manual inquiries. The automatic inquiry is made and issued by the management apparatus 100 when the case data does not satisfy the predetermined criteria as a result of the logical check performed by the management apparatus 100. On the other hand, the manual inquiry is made by a user of the management apparatus 100 or the terminal 200, registered in the management apparatus 100, and issued by the management apparatus 100.

In the description below, an inquiry means a collective name for automatic inquiry and manual inquiry. An inquiry is differentiated into an automatic inquiry or a manual inquiry if necessary.

To close an inquiry means to end the inquiry. For example, to close an inquiry means that an inquiry is retrieved from an inquiry list described below, which is displayed to a user, or deleted, and an answer to the inquiry becomes unnecessary.

Here, for example, when the management apparatus 100 receives an answer to one inquiry from a physician-in-charge via the terminal 200, the management apparatus 100 closes the one inquiry. Further, the management apparatus 100 re-performs the logical check on the basis of the answer to the one inquiry. As a result of the logical check, if a cause of another inquiry is solved, the management apparatus 100 makes an answer to the other inquiry and closes the other inquiry.

In the description below, ending of one inquiry, the answer to which is received from a user, is simply referred to as close in the manner as described above. On the other hand, ending of another inquiry which satisfies the predetermined criteria in the logical check re-performed on the basis of the answer to the one inquiry is referred to as automatic close.

In the embodiment, the close or the automatic close is set to end the automatic inquiry, and, to end the manual inquiry, only the close is set and the automatic close is not set. Therefore, regarding the manual inquiry of the embodiment, even when the cause of the inquiry is solved by the re-performed logical check, the inquiry is not automatically closed.

(2-2) Basic Processing

Hereinafter, basic processing for explaining an outline of the embodiment will be described with reference to FIGS. 2 and 3.

Figure 2:
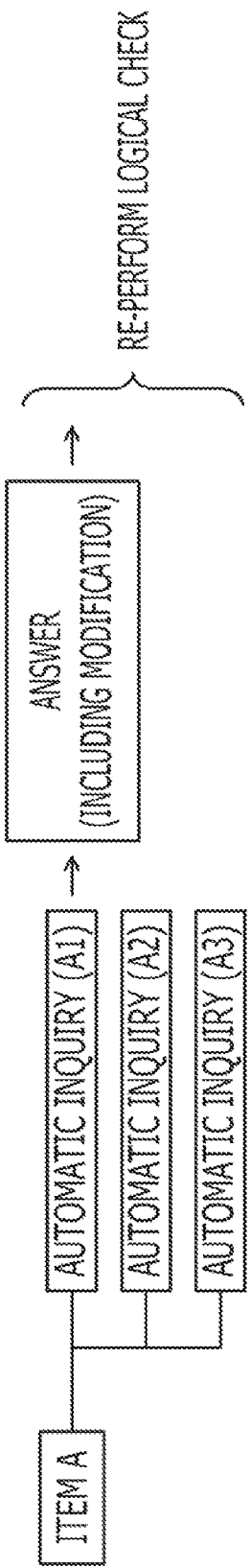
FIG. 2 is an illustration showing a relationship between an item and automatic inquiries.
Figure 3:
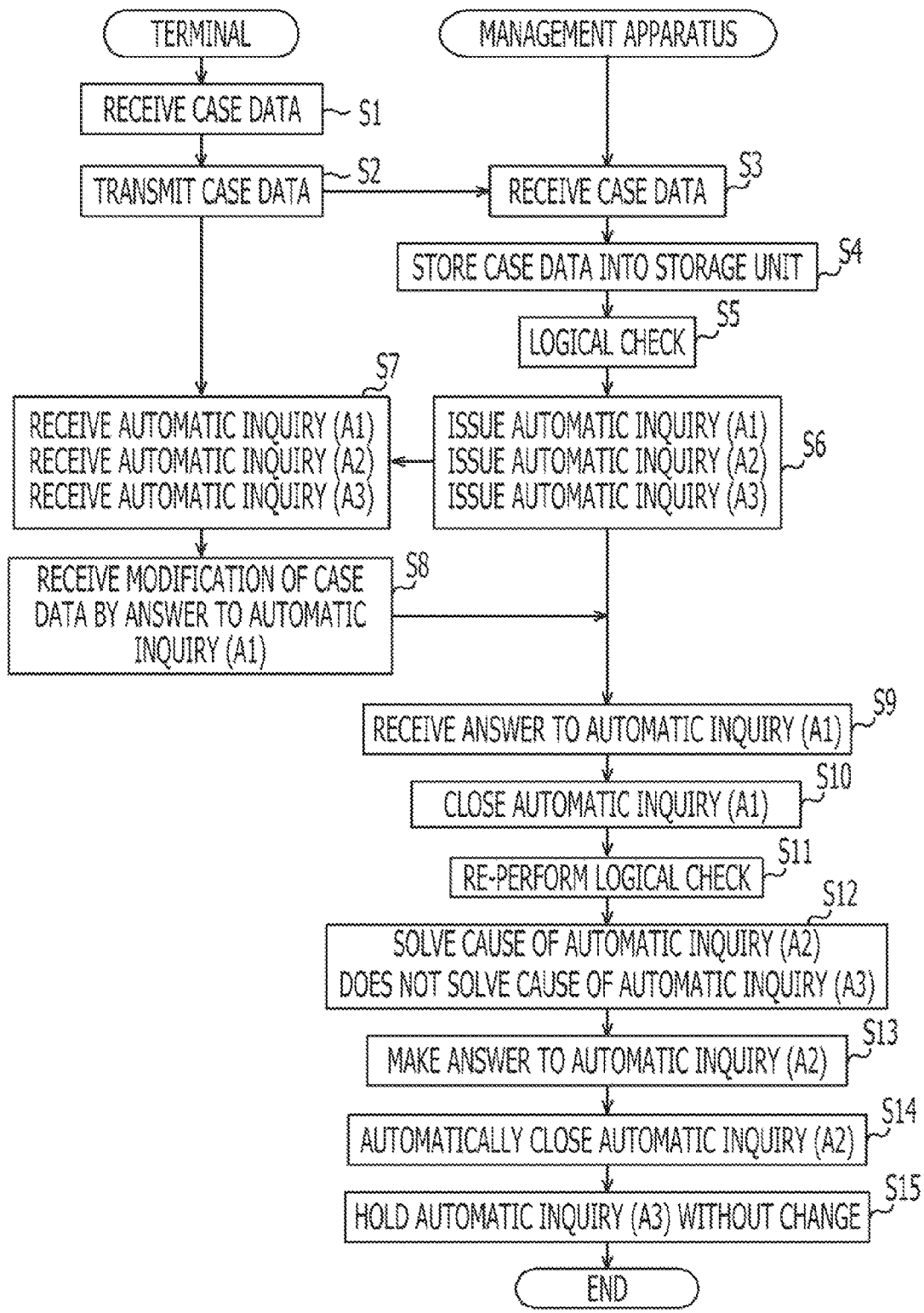
FIG. 3 is an example of a flowchart showing processing from receiving case data to making an answer to an automatic inquiry.

FIG. 2 is an illustration showing a relationship between an item and automatic inquiries. FIG. 3 is an example of a flowchart showing a flow from receiving case data to making an answer to an automatic inquiry.

Here, for the sake of simplicity, an example in which there are a plurality of automatic inquiries with respect to a single item is used. As shown in FIG. 2, the management apparatus 100 issues three automatic inquiries (A1) to (A3) with respect to case data of item A. In other words, the item of the automatic inquiries (A1) to (A3) is the item A common to all the automatic inquiries.

A flow from receiving case data to making an answer to an automatic inquiry will be described with reference to FIGS. 2 and 3.

Operation S1, Operation S2: The terminal 200 receives case data from a physician-in-charge (Operation S1), and transmits the case data to the management apparatus 100 (Operation S2).

Operation S3, Operation S4: When the management apparatus 100 receives the case data from the terminal 200 (Operation S3), the management apparatus 100 stores the case data into a case data storage unit 8 described below (Operation S4).

Operation S5: Next, the management apparatus 100 performs a logical check for testing whether or not the case data stored in the case data storage unit 8 satisfies the predetermined criteria for each item in the case report form.

Operation S6: As shown in FIG. 2, the management apparatus 100 issues three automatic inquiries (A1) to (A3) with respect to the item A on the basis of the result of the logical check in S5.

For example, it is assumed that the item A is a body height, and, as predetermined criteria with respect to the item A, there are three criteria, which are a first criterion that the type of data is "numerical value", a second criterion that the maximum number of digits is "3", and a third criterion that the allowed range is "0 to 200 cm". Here, it is assumed that the case data actually inputted into the item A is "#210" in which a symbol and a numerical value coexist. The management apparatus 100 issues the automatic inquiry (A1) because the case data of the item A does not satisfy the first criterion, issues the automatic inquiry (A2) because the case data does not satisfy the second criterion, and issues the automatic inquiry (A3) because the case data does not satisfy the third criterion.

Operation S7: The terminal 200 receives the three automatic inquiries (A1) to (A3) with respect to the item A. Further, the terminal 200 displays the three automatic inquiries (A1) to (A3), for example, on a display as an inquiry list.

Operation S8: Next, the terminal 200 receives answers to the automatic inquiries (A1) to (A3) from the physician-in-charge.

Here, it is possible to answer each inquiry individually, and first, the physician-in-charge selects an inquiry to be answered first from the three automatic inquiries (A1) to (A3). In FIGS. 2 and 3, the physician-in-charge selects the automatic inquiry (A1) and answers the automatic inquiry (A1).

The terminal 200 receives, for example, a modification of the case data of the item A as an answer to the automatic inquiry (A1). Here, it is assumed that the terminal 200 receives a modification in which the case data of the item A is modified from "#210" to "210" as an answer to the automatic inquiry (A1).

Operation S9: The management apparatus 100 receives the answer to the automatic inquiry (A1), and modifies the case data stored in the case data storage unit 8 according to the modification included in the answer.

Operation S10: The management apparatus 100 closes the automatic inquiry (A1) because the answer is received. The management apparatus 100 closes the automatic inquiry (A1) whether or not the modified case data satisfies the first criterion of the automatic inquiry (A1) because the answer to the automatic inquiry (A1) is received.

Operation S11: Next, the management apparatus 100 re-performs the logical check on the basis of the modified case data. At this time, as shown in FIG. 2, the management apparatus 100 re-performs the logical check with respect to only the item A common to the automatic inquiries (A1) to (A3).

Operation S12: In the modified case data, "210" satisfies the first criterion that the type of data is "numerical value" and the second criterion that the maximum number of digits is "3". However, in the modified case data, "210" does not satisfy the third criterion that the allowed range is "0 to 200 cm". Therefore, the management apparatus 100 determines that the cause of the automatic inquiry (A2) is solved, but the cause of the automatic inquiry (A3) is not solved.

Operation S13: The management apparatus 100 makes an answer to the automatic inquiry (A2), whose cause is solved, on the basis of the automatic inquiry (A1). The answer to the automatic inquiry (A2) is, for example, an answer as described below.

An example of the answer to the automatic inquiry (A2): "In the answer to the automatic inquiry (A1), the case data of the item A is modified from "#210" to "210", and as a result, the cause of the automatic inquiry (A2) is solved, so that the automatic inquiry (A2) is automatically closed".

Operation S14, Operation S15: The management apparatus 100 automatically closes the automatic inquiry (A2) whose cause is solved, and holds the automatic inquiry (A3) whose cause is not solved without change.

When an answer to one inquiry solves a cause of another inquiry, the management apparatus 100 makes an answer to the other inquiry. Thus, it saves time and effort for the user to make an answer to the other inquiry. Therefore, an operation to make an answer to an inquiry can be performed efficiently and quickly.

When an answer to one inquiry solves a cause of another inquiry, the management apparatus 100 automatically closes the other automatic inquiry as shown in operation S14 because the other inquiry is an automatic inquiry. Here, if the automatic inquiry is automatically closed and an answer to the automatic inquiry is not made, it is difficult to analyze and understand the reason why the automatic inquiry is automatically closed. However, even when the other inquiry is automatically closed, the management apparatus 100 according to the embodiment makes and holds an answer to the other inquiry as shown in operation S13 described above. Therefore, it is easy for an administrator of the management apparatus 100 and a system including the management apparatus 100 and a person-in-charge of clinical trial to perform a follow-up investigation of an inquiry, or it is easy for an auditor from outside, such as the Ministry of Health, Labour and Welfare to perform a follow-up investigation of an inquiry.

In operation S10, the automatic inquiry (A1) is closed before the logical check is re-performed. However, when the management apparatus 100 determines again that the modified case data does not satisfy the first criteria in the re-performed logical check, the management apparatus 100 issues the automatic inquiry (A1) again.

(2-3) Range in which Logical Check is Re-Performed

Next, a range in which the logical check is re-performed will be further described. The range in which the logical check is re-performed corresponds to the item related to the inquiry to which an answer is made. More specifically, the logical check is re-performed on the item to which an answer is made. For example, in the example of FIG. 2 described above, the management apparatus 100 re-performs the logical check with respect to the item A only. As a result of the logical check, when the management apparatus 100 determines that the case data satisfies a predetermined criterion of another inquiry, the management apparatus 100 makes an answer to the other inquiry on the basis of the answer to the one inquiry.

In the basic processing of (2-1) described above, an example in which there are a plurality of inquiries with respect to a single item A is described. In the description below, in order to further explain the range in which the logical check is re-performed, an example in which there are a plurality of inquiries with respect to a plurality of items will be used.

Figure 4:
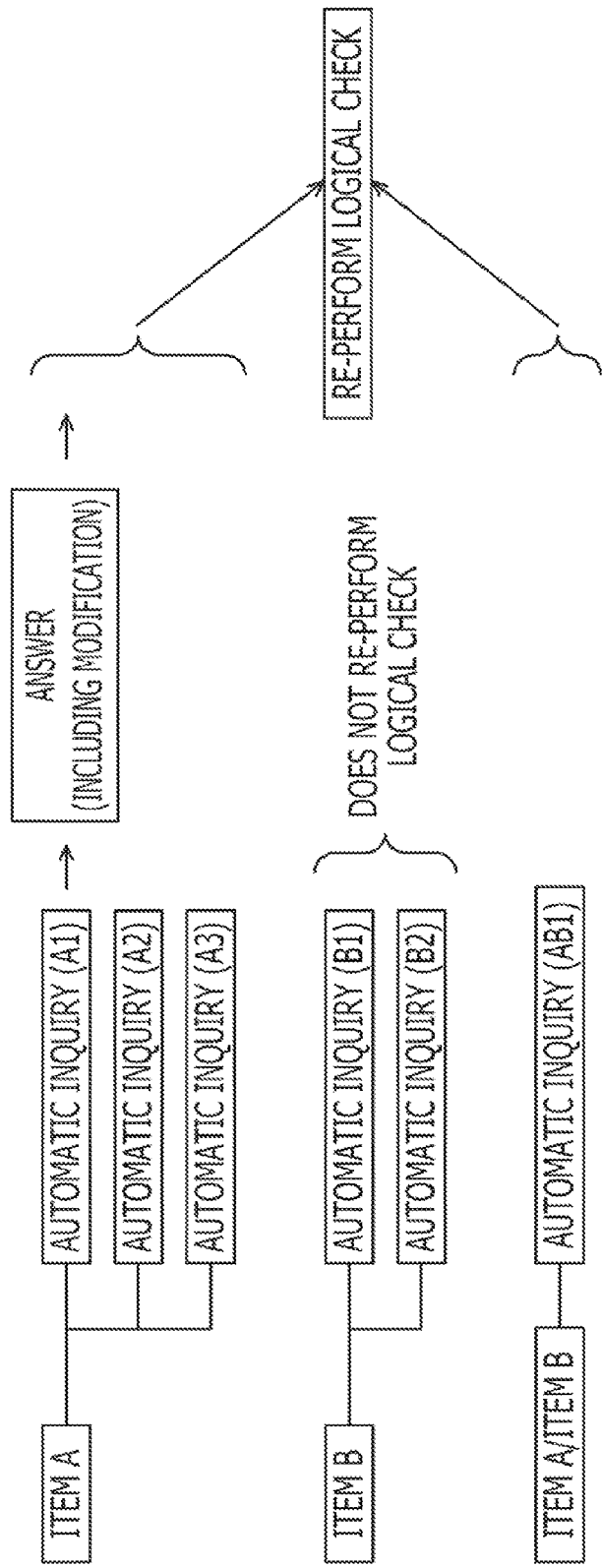
FIG. 4 is an illustration showing a first example of a case in which there are a plurality of inquiries with respect to a plurality of items.
Figure 5:
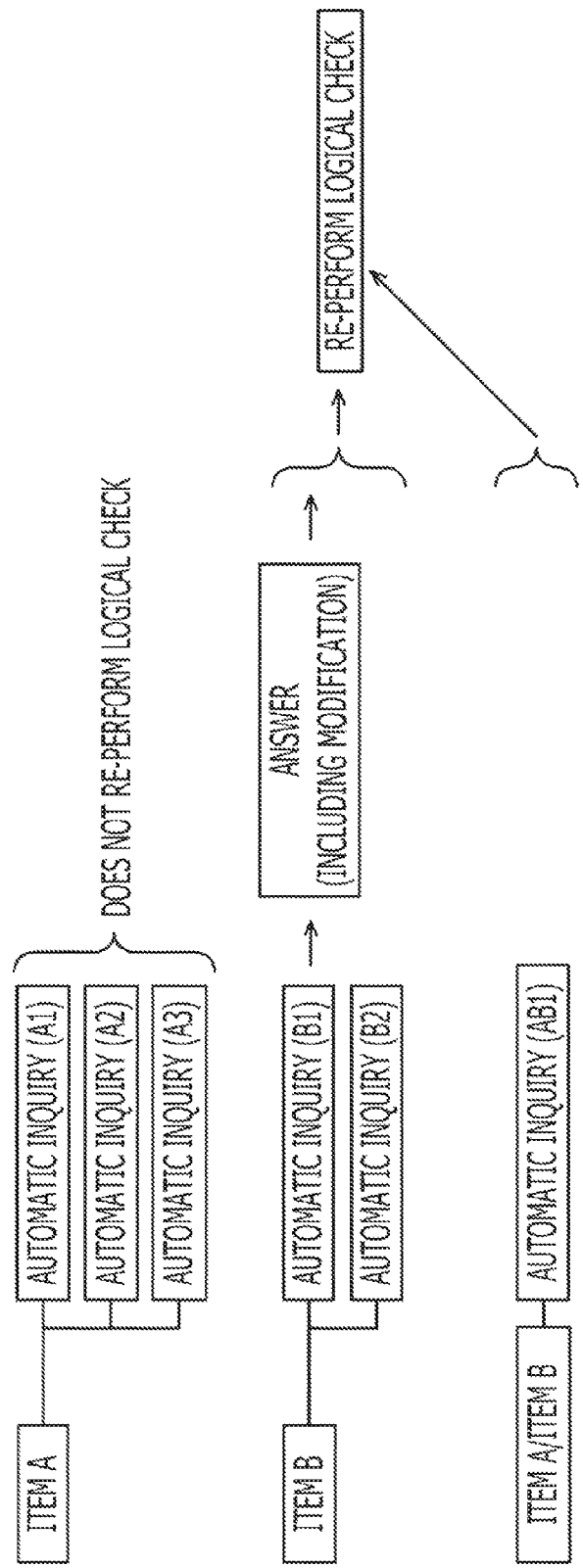
FIG. 5 is an illustration showing a second example of a case in which there are a plurality of inquiries with respect to a plurality of items.
Figure 6:
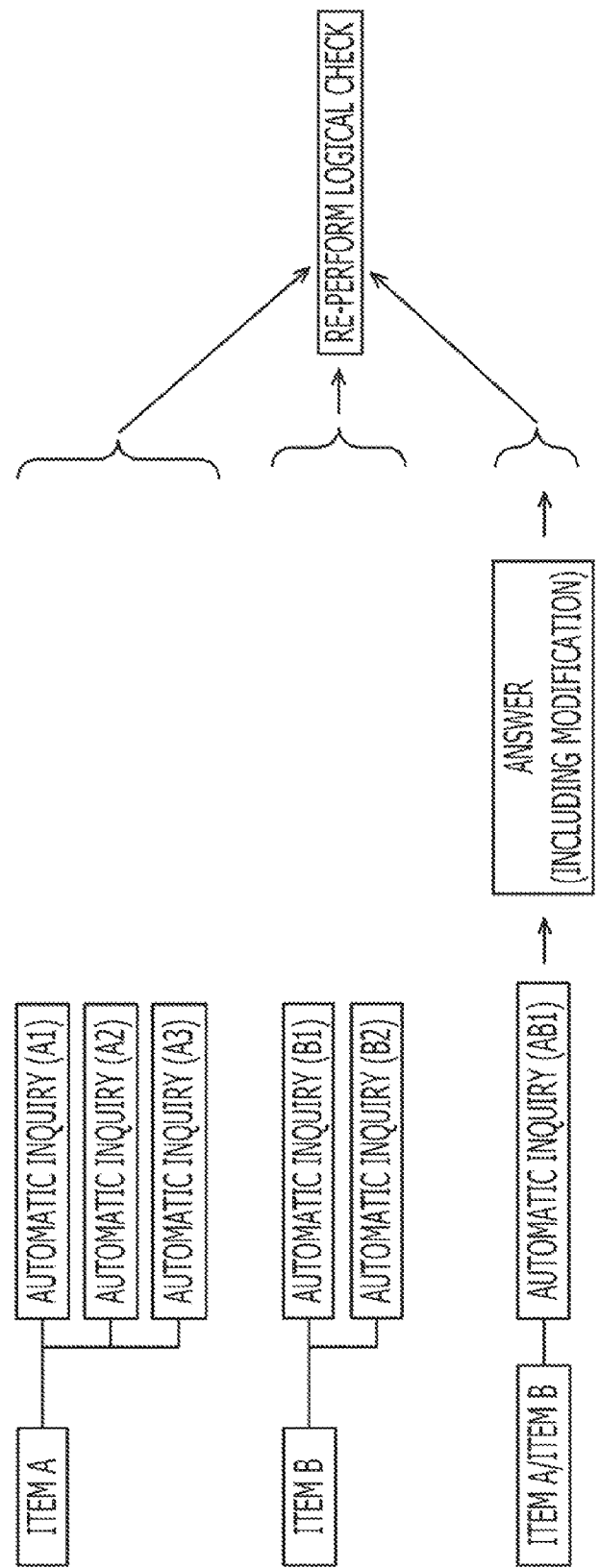
FIG. 6 is an illustration showing a third example of a case in which there are a plurality of inquiries with respect to a plurality of items.

FIGS. 4 to 6 are illustrations showing a plurality of examples of a case in which there are a plurality of inquiries with respect to a plurality of items.

In FIGS. 4 to 6, the management apparatus 100 issues three automatic inquiries (A1) to (A3) with respect to case data of item A, and issues two automatic inquiries (B1) to (B2) with respect to case data of item B. Further, the management apparatus 100 issues one automatic inquiries (AB1) with respect to case data of item A/item B. Here, the item A/item B is a criterion that defines a relationship between the item A and the item B, such as a magnitude relation between the item A and the item B, and a relational expression between the item A and the item B. Therefore, an inquiry with respect to the item A/item B is an inquiry with respect to a relationship between the case data of the item A and the case data of the item B.

Here, as shown in FIG. 4, it is assumed that the management apparatus 100 receives an answer to the automatic inquiry (A1), which includes a modification of the case data of the item A. In this case, the management apparatus 100 re-performs the logical check with respect to the modified item A and the item A/item B including the item A.

On the other hand, as shown in FIG. 5, it is assumed that the management apparatus 100 receives an answer to the automatic inquiry (B1), which includes a modification of the case data of the item B. In this case, the management apparatus 100 re-performs the logical check with respect to the modified item B and the item A/item B including the item B.

Further, as shown in FIG. 6, it is assumed that the management apparatus 100 receives an answer to the automatic inquiry (AB1), which includes a modification of both the case data of the item A and the case data of the item B. In this case, the management apparatus 100 re-performs the logical check with respect to the item A, the item B, and the item A/item B. In addition, for example, if the management apparatus 100 receives an answer to the automatic inquiry (AB1), which includes a modification of the case data of the item A only, the management apparatus 100 re-performs the logical check with respect to the item A and the item A/item B.

As shown in FIGS. 4 to 6, the range in which the logical check is re-performed corresponds to the item related to the inquiry to which an answer is made. Therefore, the management apparatus 100 does not re-perform the logical check with respect to an item that is not related to the item to which an answer is made, so that it is possible to improve processing efficiency of the logical check.

When the answer to an inquiry does not include a modification of the case data, the management apparatus 100 does not re-perform the logical check. This will be described below with reference to FIG. 2 described above and FIG. 7.

Figure 7:
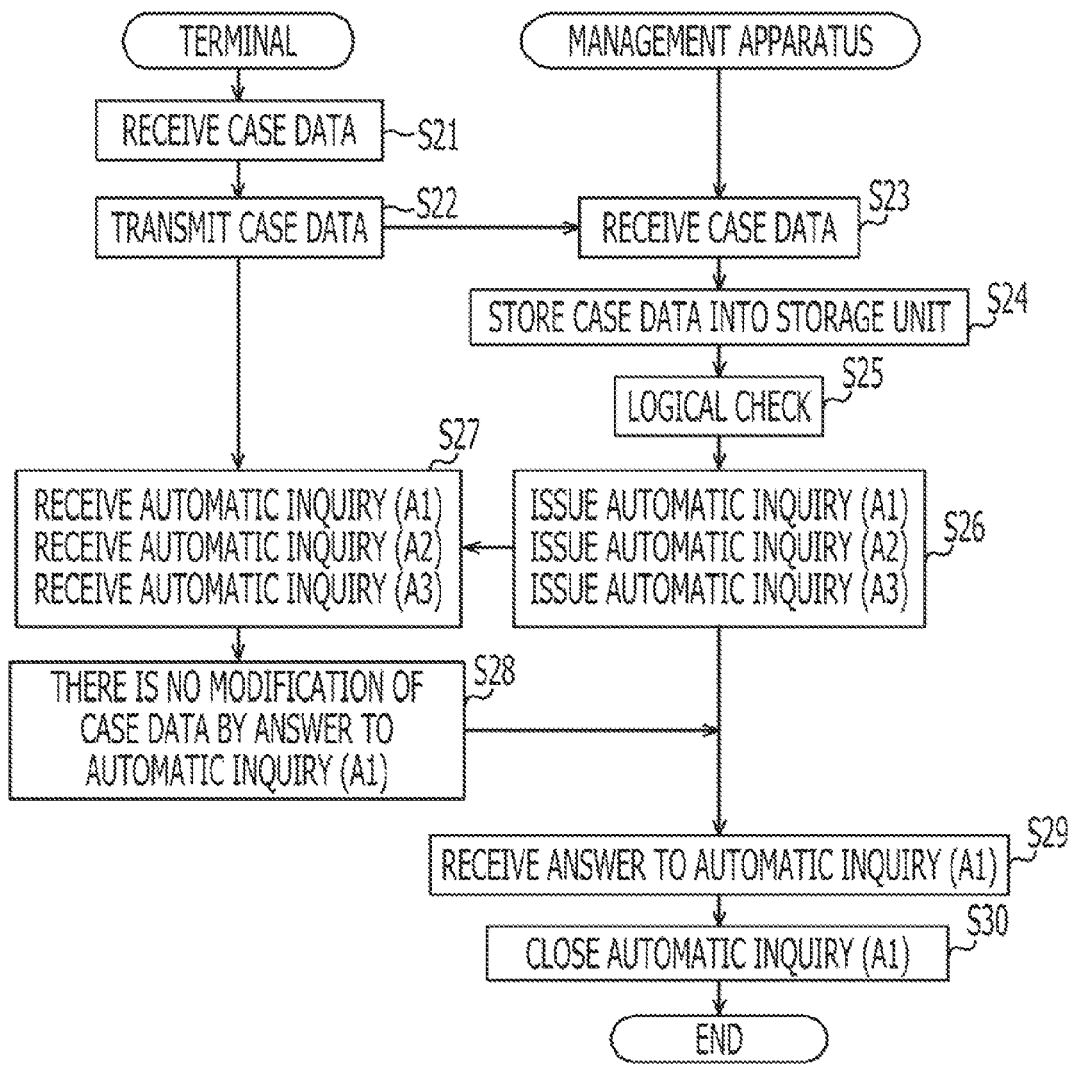
FIG. 7 is an example of a flowchart showing processing from receiving case data to making an answer to an inquiry when a logical check is not re-performed.

FIG. 7 is an example of a flowchart showing a flow from receiving case data to making an answer to an inquiry when the logical check is not re-performed.

Operation S21 to Operation S27: In the same manner as in operation S1 to operation S7 of FIG. 3 described above, the three automatic inquiries (A1) to (A3) with respect to the item A are issued as shown in FIG. 2. The terminal 200 displays the three automatic inquiries (A1) to (A3), for example, on a display as an inquiry list.

Operation S28: The terminal 200 receives an answer to the automatic inquiry (A1) from the physician-in-charge. At this time, it is assumed that there is no modification of the case data of the item A.

Operation S29: The management apparatus 100 receives an answer to the automatic inquiry (A1). However, the answer does not include a modification of the case data, so that the management apparatus 100 does not modify the case data in the case data storage unit 8.

Operation S30: The management apparatus 100 closes the automatic inquiry (A1). Here, in operation S28, there is no modification of the case data, and thus the management apparatus 100 does not re-perform the logical check. Therefore, the automatic inquiry (A2) and the automatic inquiry (A3) are held without change.

The reason why the logical check is not re-performed is because there is no modification of the case data and there is no difference between the result of the re-performed logical check and the result of the first logical check, so that it is meaningless to re-perform the logical check.

(2-4) About Answer to Manual Inquiry

Here, when the management apparatus 100 re-performs the logical check on the basis of an answer to one inquiry, and as a result of the logical check, a cause of another automatic inquiry is solved, the management apparatus 100 makes an answer to the other automatic inquiry and automatically closes the other automatic inquiry. However, when the other inquiry is a manual inquiry, the management apparatus 100 does not make an answer to the manual inquiry, nor does it automatically close the manual inquiry. This will be described with reference to FIG. 8.

Figure 8:
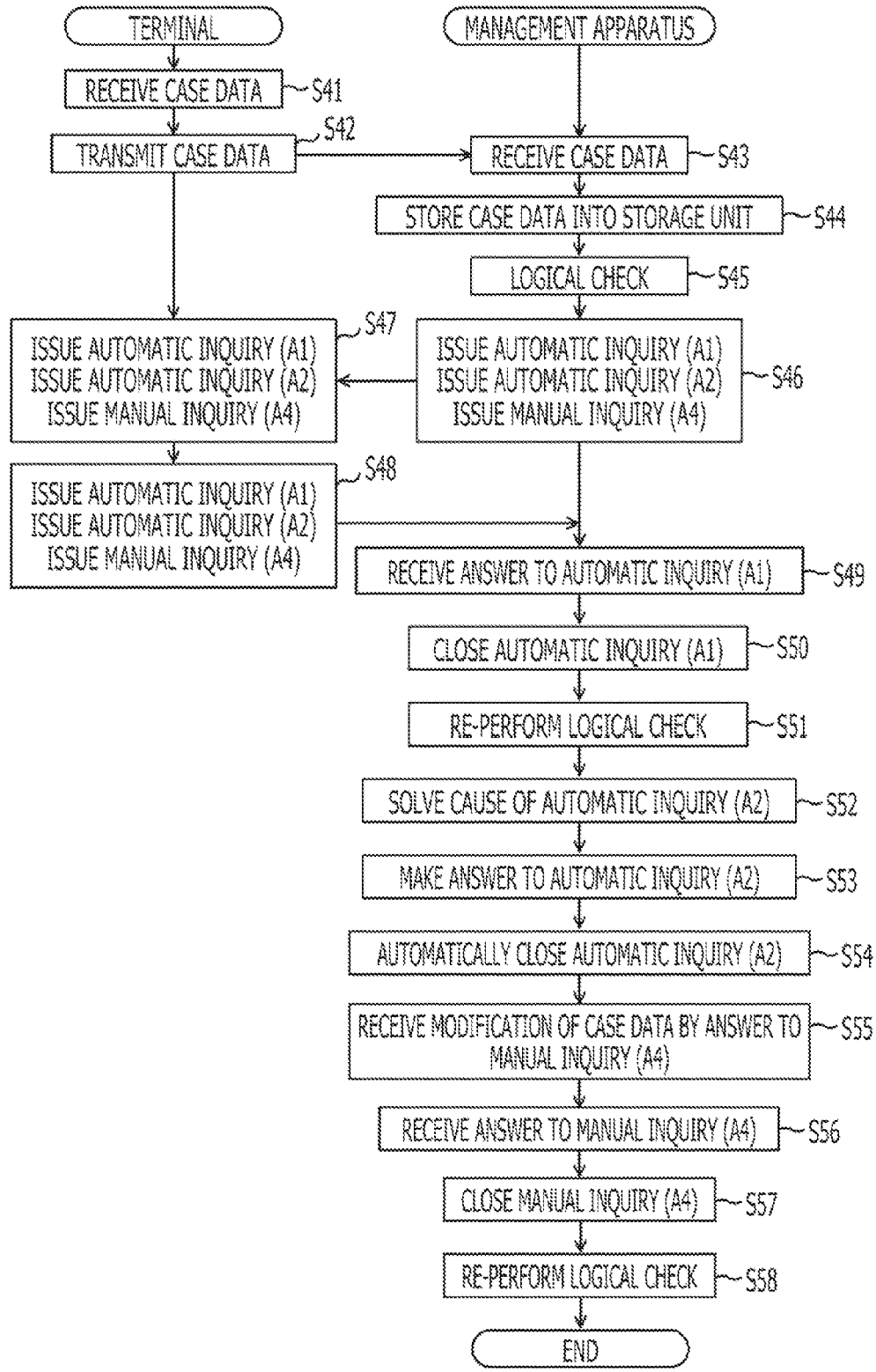
FIG. 8 is an example of a flowchart showing processing from receiving case data to making an answer to an inquiry in inquiries including a manual inquiry.

FIG. 8 is an example of a flowchart showing a flow from receiving case data to making an answer to an inquiry in inquiries including a manual inquiry.

Operation S41 to Operation S47: In the same manner as in operation S1 to operation S7 of FIG. 3 described above, the three inquiries with respect to the item A are issued. The three inquiries are, respectively, the automatic inquiry (A1), the automatic inquiry (A2), and a manual inquiry (A4). For example, the terminal 200 displays an inquiry list including the three inquiries on a display.

Operation S48: The terminal 200 receives an answer to the automatic inquiry (A1) from the physician-in-charge.

Operation S49, Operation S50: The management apparatus 100 receives an answer to the automatic inquiry (A1), which includes a modification of the case data (Operation S49), and closes the automatic inquiry (A1) (Operation S50). At this time, the management apparatus 100 modifies the case data stored in the case data storage unit 8 according to the modification included in the answer.

Operation S51: Next, the management apparatus 100 re-performs the logical check on the basis of the modified case data.

Operation S52 to Operation S54: When the management apparatus 100 determines that the cause of the automatic inquiry (A2) is solved as a result of the re-performed logical check (S52), the management apparatus 100 makes an answer to the automatic inquiry (A2) on the basis of the answer to the automatic inquiry (A1) (Operation S53). Further, the management apparatus 100 automatically closes the automatic inquiry (A2) whose cause is solved (Operation S54).

Here, regarding the manual inquiry (A4) made by a user, even when the case data thereof satisfies a predetermined criterion as a result of the re-performed logical check, the management apparatus 100 does not make an answer. Nor does it automatically close the manual inquiry (A4).

Operation S55: Next, the terminal 100 receives an answer including a modification of the case data from the physician-in-charge as an answer to the automatic inquiry (A4).

Operation S56, Operation S58: The management apparatus 100 receives an answer to the manual inquiry (A4) (Operation S56), and closes the manual inquiry (A4) (Operation S57). At this time, the management apparatus 100 modifies the case data stored in the case data storage unit 8 according to the modification included in the answer, and re-performs the logical check (Operation S58). Thereafter, the management apparatus 100 determines whether or not there is a new inquiry on the basis of the result of the re-performed logical check.

As described above, while the management apparatus 100 of the embodiment sets an automatic close to an automatic inquiry, the management apparatus 100 makes an answer to an automatic inquiry before closing the automatic inquiry. Therefore, if the management apparatus 100 of the embodiment is used, even when an automatic inquiry is automatically closed due to the solution of the cause thereof, traceability of the automatic inquiry is improved.

EXAMPLE

Hereinafter, a specific example will be described.

(1) Network Configuration

As shown in FIG. 1 described above, the management system 1000 includes the management apparatus 100 and the terminal 200 installed in a medical facility. The management apparatus 100 and the terminal 200 are connected via a network 50. Examples of the management system 1000 include an EDC (Electronic Data Capture) system.

(2) Hardware Configuration

Figure 9:
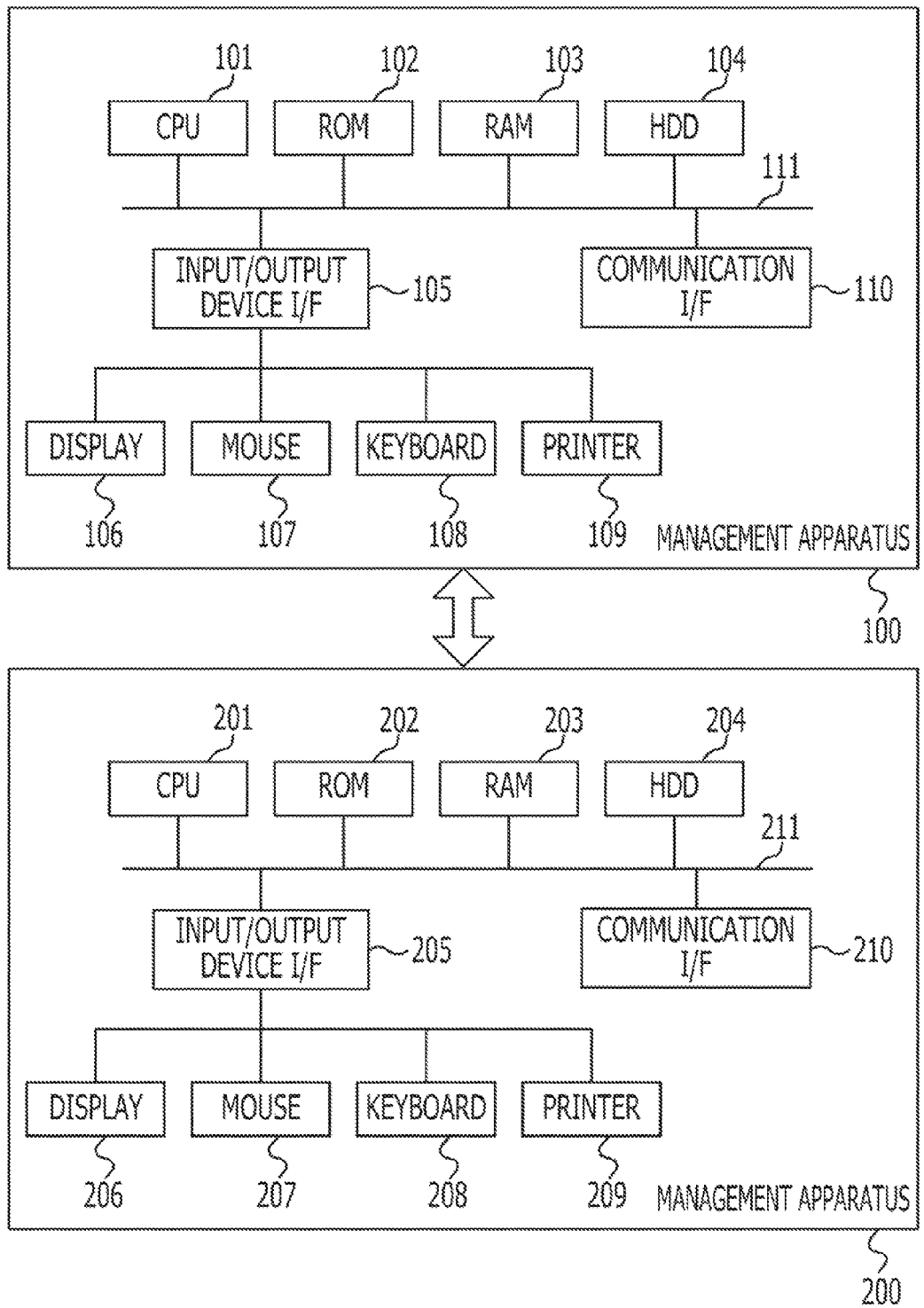
FIG. 9 is hardware configuration diagrams of a management apparatus and a terminal.

FIG. 9 is an example of a block diagram showing a hardware configuration of the management apparatus and the terminal.

(2-1) Management Apparatus

The management apparatus 100 includes, for example, a CPU (Central Processing Unit) 101, a ROM (Read Only Memory) 102, a RAM (Random Access Memory) 103, an HDD (Hard Disk Drive) 104, an input/output device I/F (InterFace) 105, and a communication I/F 110. These are connected to each other via a bus 111.

The input/output device I/F 105 is connected to input/output devices such as a display 106, a mouse 107, a keyboard 108, and a printer 109, and for example, controls the input/output devices according to instructions from the CPU 101.

The ROM 102 stores various control programs related to various controls described below, which are performed by the management apparatus 100. The various control programs include, for example, a management program described below.

The HDD 104 stores various data related to case data such as a case report form.

The RAM 103 temporarily stores the various control programs stored in the ROM 102 and information stored in the HDD 104. Further, the RAM 103 temporarily stores information such as various flags in accordance with execution of various control programs.

The CPU 101 develops the various control programs stored in the ROM 102 in the RAM 103 and performs various controls. Specifically, the CPU 101 executes a management program. For example, the CPU 101 performs a logical check, issues an inquiry, modifies case data in accordance with an answer, makes an answer to an inquiry, closes an inquiry, and automatically closes an inquiry.

The communication I/F 111 performs communication such as transmission/reception of commands or data to/from the terminal 200 on the basis of the control of the CPU 101.

(2-2) Terminal

The hardware configuration of the terminal 200 is the same as that of the management apparatus 100. For example, the terminal 200 includes a CPU 201, a ROM 202, a RAM 203, an HDD 204, an input/output device I/F 205, and a communication I/F 210. These are connected to each other via a bus 211.

The ROM 202 stores various control programs related to various controls described below, which are performed by the terminal 200.

The input/output device I/F 205 is connected to input/output devices such as a display 206, a mouse 207, a keyboard 208, and a printer 209, and for example, controls the input/output devices according to instructions from the CPU 201. The physician-in-charge inputs case data and an answer to an inquiry by operating the mouse 207, the keyboard 208, and the like.

The HDD 204 stores various data related to case data.

The RAM 203 temporarily stores the various control programs stored in the ROM 202 and information stored in the HDD 204. Further, the RAM 203 temporarily stores information such as various flags in accordance with execution of various control programs.

The CPU 201 develops the various control programs stored in the ROM 202 in the RAM 203 and performs various controls. Specifically, the CPU 201 executes various control programs. For example, the CPU 201 receives an automatic inquiry and a manual inquiry from the management apparatus 100, displays an inquiry list on the display 106, and outputs the inquiry list to the printer 209.

The communication I/F 111 performs communication such as transmission/reception of commands or data to/from the management apparatus 100 on the basis of the control of the CPU 201.

(3) Functional Configuration

Next, functional configurations of the management apparatus 100 and the terminal 200 will be described.

First, the functional configuration of the management apparatus 100 will be described.

(3-1) Management Apparatus

FIG. 10 is an example of a block diagram showing the functional configuration of the management apparatus according to the example.

Processing of each functional unit of the management apparatus 100 is performed by the CPU 101, the ROM 102, the RAM 103, the HDD 104, the input/output device I/F 105, the communication I/F 110, and the like which cooperate with each other. Further, the processing described below is performed by performing the management program stored in the ROM 102 in the management apparatus.

The functional units of the management apparatus 100 include, for example, a transmitting/receiving unit 1, an input/output receiving unit 2, a determination unit 3, an inquiry making unit 4, an answer receiving unit 5, a modification unit 6, an answer making unit 7, a case data storage unit 8, a definition table 9, an inquiry storage unit 10, and a phrase storage unit 11.

The transmitting/receiving unit 1 transmits and receives case data, an inquiry, an answer to the inquiry, various commands, and the like to and from the terminal 200.

The input/output receiving unit 2 receives case data which the terminal 200 receives from the physician-in-charge from the terminal 200 and stores the case data into the case data storage unit 8.

Further, the input/output receiving unit 2 reads an automatic inquiry made by the inquiry making unit 4 and a manual inquiry made by a user from the inquiry storage unit 10, and transmits them to the terminal 200 via the transmitting/receiving unit 1.

The case data storage unit 8 stores case data to be inputted into each item in the case report form.

FIG. 11 is an example of the case data stored in the case data storage unit. In the case data storage unit 8, for example, items, which are sub-categories, are provided for each category into which the case data is largely classified. The case data storage unit 8 stores case data in each item. Examples of the categories include human subject information related to a human subject of the clinical trial, information of clinical trial facility, clinical trial content, drug used in the clinical trial, diagnostic interview/test which is information related to a result of diagnostic interview by physician-in-charge and a result of test, and test facility information.

Examples of the items in the human subject information include human subject ID for identifying a human subject, case number provided for each human subject and each clinical trial, disorder content, birth date of the human subject, age, sex, body height, and body weight.

Examples of the items in the information of clinical trial facility include name of clinical trial execution facility and name of physician-in-charge.

Examples of the items in the clinical trial content include a method of clinical trial and a clinical trial start date.

Examples of the items in the drug include name of used drug, drug administration date, and drug-taking condition.

Examples of the items in the diagnostic interview/test include date of diagnostic interview (visit) which is a visit date of the human subject, result of diagnostic interview, date of test request to test facility, sample collection date, test content, and test result. Further, the item of the result of diagnostic interview is divided into detailed categories such as, for example, systolic blood pressure and diastolic blood pressure so that the result of diagnostic interview can be written in detail. Also, the item of the test content is divided into detailed categories such as the number of red blood cells and the number of white blood cells so that the test result can be written in detail.

Examples of the items in the test facility information include name of test execution facility and test execution date.

In the example of FIG. 11, the case data storage unit 8 stores, for example, information described below with respect to a human subject with a human subject ID "h-0001". The information indicates that the clinical trial start date is "Nov. 10, 2009", the date of diagnostic interview is "Nov. 15, 2009", the systolic blood pressure is "100" mmHg, and the diastolic blood pressure is "100" mmHg. Also, the case data storage unit 8 stores, for example, information described below with respect to a human subject with a human subject ID "h-0002". The information indicates that the clinical trial start date is "Dec. 10, 2009", the date of diagnostic interview is "Dec. 20, 2009", the systolic blood pressure is "150" mmHg, the diastolic blood pressure is "85" mmHg, the number of red blood cells is "5,000,000"/mm$^3$, and the number of white blood cells is "2,000"/mm$^3$.

Regarding the items in the case data storage unit 8, attributes, which indicate which case data should be inputted into which item, whether or not the item is an input required item, and the like, are defined for each item. The definition table 9 stores definition of the attributes of the items.

FIG. 12 is an example of the definition table. In the definition table 9 of FIG. 12, for example, data type, the number of digits, allowed value range, relationship between items, and the like are defined for each item. The data type indicates a type of value, such as alphanumeric characters, text, date, and numerical value, which can be inputted into an item. The number of digits indicates the maximum number of digits that can be inputted. The allowed value range indicates a normal range of a value of the case data in the item when the case data is normal. The relationship between items indicates a magnitude relation among a plurality of items, a mathematical expression that must be satisfied by a plurality of items, and the like.

In addition, the attributes defined for items includes a setting of an input required item or an optional input item, a setting of the number of required digits after the decimal point, and the like.

In the definition table 9 of FIG. 12, for example, the attributes of the systolic blood pressure are defined such that the data type is "numerical value", the maximum number of digits is "3", the allowed value range is "110 to 180" mmHg, and the relationship between items is "systolic blood pressure>diastolic blood pressure". Here, the attributes such as the data type, the number of digits, the allowed value range, and the relationship between items, which are defined for one item, are respectively the criteria that define the attributes of the item. In other words, in a case of the systolic blood pressure, a first criterion is that the data type is "numerical value", a second criterion is that the maximum number of digits is "3", a third criterion is that the allowed value range is "110 to 180" mmHg, and a fourth criterion is that the relationship between items is "systolic blood pressure>diastolic blood pressure".

The attributes of the diastolic blood pressure are defined such that the data type is "numerical value", the maximum number of digits is "3", the allowed value range is "50 to 100" mmHg, and the relationship between items is "systolic blood pressure>diastolic blood pressure". In addition, for example, the attributes of the body height are defined such that the data type is "numerical value", the maximum number of digits is "3", and the allowed value range is "0 to 200" cm.

The determination unit 3 determines whether or not case data satisfies predetermined criteria defined in the definition table 9 for each case data in the items in the case data storage unit 8. For example, the determination unit 3 reads case data of a certain item from the case data storage unit 8. The determination unit 3 reads criteria that define attributes of the item, and compares the case data and the attributes. This test is referred to as a logical check. Although the timing of the logical check is not limited, for example, the logical check is performed every time the input/output receiving unit 2 receives case data and the case data is stored in the case data storage unit 8.

Next, an example of the logical check performed by the determination unit 3 will be described. For example, it is assumed that the determination unit 3 reads "100" mmHg as the case data of the item of the systolic blood pressure and "100" mmHg as the case data of the item of the diastolic blood pressure with respect to the human subject whose human subject ID is "h-0001". The determination unit 3 reads the first to the fourth criteria described above as the attributes of the systolic blood pressure from the definition table 9. The first criterion is that the data type is "numerical value", the second criterion is that the maximum number of digits is "3", the third criterion is that the allowed value range is "110 to 180" mmHg, and the fourth criterion is that the relationship between items is "systolic blood pressure>diastolic blood pressure".

Further, the determination unit 3 compares the systolic blood pressure "100" mmHg and the diastolic blood pressure "100" mmHg with the first to the fourth criteria, and determines whether or not the case data satisfies the criteria. As a result, the determination unit 3 obtains a first logical check result indicating that the systolic blood pressure "100" mmHg and the diastolic blood pressure "100" mmHg are not in a relationship of "systolic blood pressure>diastolic blood pressure". Further, the determination unit 3 obtains a second logical check result indicating that the systolic blood pressure "100" mmHg is not within the allowed value range "110 to 180" mmHg.

When the determination unit 3 obtains a logical check result indicating that case data of a certain item does not satisfy the attributes defined for the item, the determination unit 3 outputs the logical check result and related information to the inquiry making unit 4. Examples of the related information include the logical check item that is the target of the logical check and the error attribute where the case data does not satisfy the criterion. For example, the determination unit 3 outputs "systolic blood pressure" and "diastolic blood pressure", which are the logical check items, along with the first logical check result described above. Further, the determination unit 3 outputs "relationship between items", which is the error attribute, to the inquiry making unit 4. Also, for example, the determination unit 3 outputs "systolic blood pressure" which is the logical check item and "allowed value range" which is the error attribute along with the second logical check result described above to the inquiry making unit 4.

Further, the determination unit 3 re-performs the logical check on the basis of an instruction from the modification unit 6 described below. When the modification unit 6 described below modifies case data in the case data storage unit 8, the modification unit 6 instructs the determination unit 3 to re-perform the logical check. The determination unit 3 performs the logical check on the basis of the modified case data responding to the instruction to re-perform the logical check. The determination unit 3 outputs the result of the re-performed logical check to the inquiry making unit 4 and/or the answer making unit 7. The re-performed logical check will be described along with the description of the modification unit 6 and the answer making unit 7.

When the inquiry making unit 4 receives information indicating that case data in the case data storage unit 8 does not satisfy an attribute defined in an item attribute table, the inquiry making unit 4 makes an automatic inquiry. The inquiry making unit 4 receives a manual inquiry from a user of the management apparatus 100 or the terminal 200, or makes a manual inquiry on the basis of an instruction to make a manual inquiry. The inquiry making unit 4 stores the automatic inquiry and the manual inquiry into the inquiry storage unit 10.

FIG. 13 is an example of inquiries stored in the inquiry storage unit. Automatic inquiries of an inquiry ID "QRY-0001" and an inquiry ID "QRY-0002" will be described next. In the description below, for the sake of simplicity, the automatic inquiry of an inquiry ID "QRY-0001" is referred to as an automatic inquiry "QRY-0001".

First, the inquiry making unit 4 receives the logical check result and related information with respect to the systolic blood pressure of the above-described human subject ID "h-0001" from the determination unit 3. For example, the inquiry making unit 4 receives the first logical check result indicating that the systolic blood pressure "100" mmHg and the diastolic blood pressure "100" mmHg are not in a relationship of "systolic blood pressure>diastolic blood pressure". At this time, the inquiry making unit 4 receives "systolic blood pressure" and "diastolic blood pressure" which are the logical check items and "relationship between items" which is the error attribute along with the first logical check result from the determination unit 3. Further, the inquiry making unit 4 receives the second logical check result indicating that the systolic blood pressure "100" mmHg is not within the allowed value range "110 to 180" mmHg. At this time, the inquiry making unit 4 receives "systolic blood pressure" which is the logical check item and "allowed value range" which is the error attribute along with the second logical check result from the determination unit 3.

Next, the inquiry making unit 4 makes an inquiry on the basis of the logical check result and related information from the determination unit 3. For example, the inquiry making unit 4 makes an automatic inquiry "QRY-0001" in accordance with the first logical check result, and stores the automatic inquiry "QRY-0001" into the inquiry storage unit 10. The content of the inquiry is as follows.

The content of the automatic inquiry "QRY-0001": "The systolic blood pressure is the same as the diastolic blood pressure. Please check again."

On the basis of the logical check items received from the determination unit 3, the inquiry making unit 4 stores the systolic blood pressure "100" mmHg and the diastolic blood pressure "100" mmHg into the inquiry storage unit 10 as inquiry items of the automatic inquiry "QRY-0001". Further, the inquiry making unit 4 stores "relationship between items" as the error attribute of the automatic inquiry "QRY-0001" into the inquiry storage unit 10. When the inquiry making unit 4 makes an inquiry, the inquiry making unit 4 stores, for example, "issued" as a state of inquiry into the inquiry storage unit 10.

Here, the inquiry made by the inquiry making unit 4 is not a manual inquiry manually made by a user, but an automatic inquiry. Therefore, the inquiry making unit 4 stores "automatic" as a type of inquiry into the inquiry storage unit 10. In addition, the inquiry making unit 4 receives various information related to the inquiry from the determination unit 3, and stores the information into the inquiry storage unit 10.

Similarly, the inquiry making unit 4 makes an automatic inquiry "QRY-0002" in accordance with the second logical check result and related information, and stores the automatic inquiry "QRY-0002" into the inquiry storage unit 10. The inquiry making unit 4 stores the systolic blood pressure "100" mmHg as an inquiry item of the automatic inquiry "QRY-0002", "allowed value range" as an error attribute, "issued" as a state of inquiry, "automatic" as a type of inquiry, and the like into the inquiry storage unit 10. The content of the inquiry is as follows.

The content of the automatic inquiry "QRY-0002": "Range error"

Next, a manual inquiry "QRY-0004" will be described. The automatic inquiry "QRY-0001" and the automatic inquiry "QRY-0002" are automatic inquiries. However, an inquiry may be a manual inquiry made by a user of the management apparatus 100 or the terminal 200. For example, the inquiry making unit 4 receives an instruction to make a manual inquiry from a user of the management apparatus 100 or the terminal 200 via the transmitting/receiving unit 1. The inquiry making unit 4 makes a manual inquiry on the basis of the instruction and stores the manual inquiry into the inquiry storage unit 10. At this time, "manual" is stored into the inquiry storage unit 10 as a type of inquiry of the manual inquiry ID "QRY-0004". The inquiry making unit 4 may receive a manual inquiry from a user and store the manual inquiry into the inquiry storage unit 10 instead of making a manual inquiry on the basis of the instruction from the user.

When the inquiry making unit 4 receives an access to an inquiry from, for example, the terminal 200, the inquiry making unit 4 reads data necessary to make a search screen and an answer screen described below from the inquiry storage unit 10 and transmits the data to the terminal 200.

FIG. 14 is an example of the search screen, and FIG. 15 is an example of the answer screen. When the terminal 200 receives a search screen command to display the search screen from the physician-in-charge, the terminal 200 transmits the search screen command to the management apparatus 100. The input/output receiving unit 2 of the management apparatus 100 reads data related to an inquiry from the inquiry storage unit 10 on the basis of the search screen command, and transmits the data to the terminal 200. The terminal 200 makes the search screen shown in FIG. 14 on the basis of the data related to the inquiry, and displays the search screen on the display 206 of the terminal 200. In the upper portion of the search screen, an input field 20 for inputting a human subject number, a case number, a name of clinical trial execution facility, a type of inquiry, and an inquiry ID, and a search button 21 for performing a search are provided. When the physician-in-charge inputs values in the input field 20 and presses the search button 21, as shown in FIG. 14, an inquiry list 22 related to desired inquiries is displayed in the lower portion of the search screen.

Next, when the physician-in-charge selects a desired inquiry from the inquiry list 22 by using a selection button 23, the terminal 200 transmits a selection command to the management apparatus 100. The input/output receiving unit 2 of the management apparatus 100 reads data from the inquiry storage unit 10 on the basis of the selection command, and transmits the data to the terminal 200. The terminal 200 makes the answer screen shown in FIG. 15 on the basis of the data from the inquiry making unit 4, and displays the answer screen on the display 206 of the terminal 200.

In the upper portion of the answer screen shown in FIG. 15, an inquiry details field 24 is provided, and detailed data related to the selected inquiry is displayed. Examples of the detailed data include an inquiry ID, a type of inquiry, content of inquiry, an issuer, a date and time of issue, a human subject number, a case number, a date of diagnostic interview, and a CRF. In the lower portion of the answer screen shown in FIG. 15, an answer field 25 is provided. In the answer field 25, an answer input field 26 into which the physician-in-charge or the like inputs an answer and an inquiry item list 27 are provided. In the inquiry item list 27, values of the inquiry items before modification are displayed, and a modification check field for checking the presence or absence of modification, a non-measurement check field for checking whether or not data is measured, and input fields for inputting a modified value and a reason for the modification are provided.

FIG. 15 shows an answer screen based on the automatic inquiry "QRY-0001". Here, when referring to the inquiry storage unit 10 of FIG. 13, the inquiry items of the inquiry ID "QRY-0001" are the systolic blood pressure "100" mmHg and the diastolic blood pressure "100" mmHg. Therefore, in the answer screen in FIG. 15, "systolic blood pressure" and "diastolic blood pressure" are displayed as the inquiry items and, "100" mmHg is displayed for both items as values before modification.

The terminal 200 receives an answer to the inquiry from, for example, the physician-in-charge via the answer screen shown in FIG. 15 described above. The answer receiving unit 5 receives the answer from the terminal 200 via the transmitting/receiving unit 1. The answer receiving unit 5 stores the answer to the inquiry into the inquiry storage unit 10. Then the answer receiving unit 5 closes the inquiry and requests the modification unit 6 to modify the case data if there is a modification of the case data.

The processing of the answer receiving unit 5 will be described below with reference to FIGS. 16 and 17. FIG. 16 is an example of an answer inputted in the answer screen, and FIG. 17 is an example of the inquiry storage unit in which the answer is stored.

It is assumed that the answer screen shown in FIG. 15 is displayed on the display 206 of the terminal 200 with respect to the automatic inquiry "QRY-0001". Here, as shown in FIG. 16, the physician-in-charge who is a user of the terminal 200 inputs "Modify the systolic blood pressure" in the answer input field 26. Further, the physician-in-charge checks the modification check field in the inquiry item list 27. The physician-in-charge inputs "150" mmHg as a modified value of the systolic blood pressure, and inputs "input error" as a reason for the modification. When the physician-in-charge finishes the input of the answer, the physician-in-charge presses an answer button 28 to fix the answer, and transmits the answer to the management apparatus 100. The answer receiving unit 5 receives the input of the physician-in-charge as an answer to the automatic inquiry "QRY-0001", and stores the answer into the inquiry storage unit 10. As shown in FIG. 17, in the inquiry storage unit 10, with respect to the automatic inquiry "QRY-0001", "Modify the systolic blood pressure" is stored in the answer input field, and "systolic blood pressure" and "150" mmHg are stored in the field of modified item (1). In addition, information specifying a modifier and a modification approver who has approved the modification may be stored in the inquiry storage unit 10.

In the inquiry storage unit 10, the systolic blood pressure before modification is stored in the inquiry item field. Therefore, the value before modification is stored in the inquiry item field and the value after modification is stored in the modified item field, so that the modification history can be saved.

Since the answer receiving unit 5 receives the answer, the answer receiving unit 5 closes the automatic inquiry "QRY-0001", and as shown in FIG. 17, changes the state of inquiry form "issued" to "close".

Further, when the case data is modified by the received answer, the answer receiving unit 5 instructs the modification unit 6 to modify the case data in the case data storage unit 8. For example, it is assumed that the answer receiving unit 5 receives the answer shown in FIG. 16. In this case, the answer receiving unit 5 instructs the modification unit 6 to modify the case data on the basis that the modification check field of the systolic blood pressure is checked and the value after modification is inputted. For example, the answer receiving unit 5 issues a modification instruction indicating that "Modify "systolic blood pressure" of the human subject number "h-0001" and the date of diagnostic interview "Nov. 15, 2009" to "150" mmHg".

If the same human subject has a diagnostic interview multiple times, the case data needs to be divided into case data for each date of diagnostic interview, so that the modification instruction includes the date of diagnostic interview. In addition, the modification instruction includes any data such as a case number for specifying which data is modified in the case data storage unit 8.

The modification unit 6 modifies the case data in the case data storage unit 8 on the basis of the modification instruction from the answer receiving unit 5. In a case of the modification instruction described above based on the answer of FIG. 16, the modification unit 6 modifies the "systolic blood pressure" of the human subject number "h-0001" and the date of diagnostic interview "Nov. 15, 2009" from "100" mmHg to "150" mmHg in the case data storage unit 8 of FIG. 11.

Next, when the modification unit 6 modifies the case data, the modification unit 6 instructs the determination unit 3 to re-perform the logical check on the modified case data. The instruction to re-perform the logical check is made, for example, on the basis of the modification instruction from the answer receiving unit 5. Further, the instruction to re-perform the logical check includes the human subject number, the date of diagnostic interview, the modified item, and the like in the inquiry to which an answer including a modification is given. In a case of the modification instruction described above, the modification unit 6 instructs the determination unit 3 to re-perform the logical check on the modified case data of the human subject number "h-0001", the date of diagnostic interview "Nov. 15, 2009", and "systolic blood pressure".

In this case, first, the determination unit 3 reads "150" mmHg which is the modified case data of the human subject number "h-0001", the date of diagnostic interview "Nov. 15, 2009", and "systolic blood pressure" from the case data storage unit 8 of FIG. 11. The determination unit 3 re-performs the logical check on the "150" mmHg by referring to the definition table 9. Here, regarding the case data "150" mmHg of the modified systolic blood pressure, the data type is "numerical value", the number of digits is "3", and "150" mmHg is within the allowed value range of "110 to 180" mmHg. When referring to the case data storage unit 8 of FIG. 11, the case data of the diastolic blood pressure of the human subject number "h-0001" and the date of diagnostic interview "Nov. 15, 2009" is "100" mmHg. Therefore, the relationship of "the systolic blood pressure "150" mmHg>the diastolic blood pressure "100" mmHg" is also satisfied.

Next, the determination unit 3 determines whether or not there is another inquiry related to one inquiry to which an answer including a modification is given. For example, the determination unit 3 determines whether or not there is another inquiry having the same human subject number and the same date of diagnostic interview as those of the one inquiry and further having at least a part of inquiry items which matches those of the one inquiry. When there is the other inquiry, the determination unit 3 determines whether or not the other inquiry has been closed or has been automatically closed, and further determines whether or not the other inquiry is an automatic inquiry. If the other inquiry which has not been closed or has not been automatically closed is an automatic inquiry, the determination unit 3 determines whether or not the cause of the other inquiry is solved by re-performing the logical check.

For example, after the answer receiving unit 5 receives the answer including a modification to the automatic inquiry "QRY-0001", each case data in the inquiry storage unit 10 is in a state shown in FIG. 17. The automatic inquiry "QRY-0001" and the automatic inquiry "QRY-0002" have the common human subject number "h-0001" and the common date of diagnostic interview "Nov. 15, 2009". The inquiry items of the automatic inquiry "QRY-0001" are "systolic blood pressure" and "diastolic blood pressure", and the inquiry item of the automatic inquiry "QRY-0002" is "systolic blood pressure", so that both automatic inquiries have the same "systolic blood pressure". Therefore, as another inquiry related to the automatic inquiry "QRY-0001", there is the automatic inquiry "QRY-0002". Further, regarding the automatic inquiry "QRY-0002", the state of inquiry is "issued", the automatic inquiry is not closed or not automatically closed, and the type of inquiry is "automatic". The state of inquiry of the automatic inquiry "QRY-0001" is "close" because the answer is received from the terminal 200. Therefore, the determination unit 3 determines whether or not the cause of the automatic inquiry "QRY-0002" is solved by re-performing the logical check after the answer is given to the automatic inquiry "QRY-0001".

Here, the error attribute of the automatic inquiry "QRY-0002" is "allowed value range", and the content of the inquiry is "range error" indicating that the systolic blood pressure "100" mmHg is not within the allowed value range "110 to 180" mmHg. However, the modified systolic blood pressure "150" mmHg is within the allowed value range "110 to 180" mmHg. The determination unit 3 determines that the cause of the automatic inquiry "QRY-0002" is solved by the answer to the automatic inquiry "QRY-0001" on the basis of the result described above. On the basis of this determination result, the determination unit 3 outputs an answer making instruction to make an answer to the automatic inquiry "QRY-0002" on the basis of the answer to the automatic inquiry "QRY-0001" to the answer making unit 7.

When the determination unit 3 obtains a new result indicating that a defined attribute is not satisfied in the re-performed logical check, the determination unit 3 instructs the inquiry making unit 4 to make a new inquiry.

If a cause of another inquiry is solved on the basis of the answer to the one inquiry, the answer making unit 7 receives an answer making instruction to make an answer to the other inquiry on the basis of the answer to the one inquiry from the determination unit 3. The answer making unit 7 reads an appropriate phrase from the phrase storage unit 11 on the basis of the answer making instruction. Then the answer making unit 7 makes an answer to the other inquiry on the basis of the phrase and the answer to the one inquiry.

FIG. 18 is an example of a fixed phrase storage unit. The fixed phrase storage unit 11 stores a phrase for each phrase ID. In a case of a phrase corresponding to a phrase ID "K0001", input fields are provided in the phrase, and variables according to the answer are inputted into the input fields. The input fields include fields into which an ID number, an item, a reason for the modification, a value before modification, and a value after modification are respectively inputted.

For example, the answer making unit 7 makes an answer in a manner described below. Here, the answer making instruction is an instruction to make an answer to the automatic inquiry "QRY-0002" on the basis of the answer to the automatic inquiry "QRY-0001". The answer making unit 7 refers to the inquiry storage unit 10 and obtains data necessary to make the answer. For example, the answer making unit 7 obtains "systolic blood pressure" which is the modified item, "100" mmHg which is the value before modification, "150" mmHg which is the value after modification, "input error" which is the reason for the modification, and the like with respect to the automatic inquiry "QRY-0001".

Next, the answer making unit 7 selects an appropriate phrase from the phrase storage unit 11. For example, the answer making unit 7 determines that the case data is modified on the basis of various data obtained to make the answer. In this case, for example, the answer making unit 7 selects the phrase of the phrase ID "K0001" which has a keyword of modification. The phrase storage unit 11 may store the check in the modification check field in the answer screen and the phrase ID "K0001" in association with each other. Based on this, the answer making unit 7 can select the phrase ID "K0001" on the basis that the modification check field is checked in the answer screen of FIGS. 15 and 16.

The answer making unit 7 makes an answer to the automatic inquiry "QRY-0002" on the basis of the selected phrase and the obtained data. In a case of the phrase of the phrase ID "K0001", the answer making unit 7 makes an answer as described below by inputting the obtained data into each input field. "In the inquiry ID "QRY-0001", "systolic blood pressure" is modified from "100" to "150" due to "input error", and thus the condition of the inquiry (inquiry ID "QRY-0002") is satisfied, so that the inquiry is automatically closed."

The above-described answer specifies the inquiry such as "QRY-0001" which corresponds to an answer on the basis of which the above-described answer is made, and thereby it is possible to obtain an audit trail with high traceability. The above-described answer includes the case data before and after the modification and the reason for the modification. Therefore, it is possible to immediately know how the case data is modified and the cause of the inquiry is solved, and why the modification is required. In addition, the answer may include information specifying a modifier of the case data and an approver of the modification.

The answer making unit 7 stores the answer to the automatic inquiry "QRY-0002" into the inquiry storage unit 10. Then, answer making unit 7 automatically closes the automatic inquiry "QRY-0002". FIG. 19 is an example of the inquiry storage unit in which the answer to the automatic inquiry "QRY-0002" is stored. The above described answer is stored in the answer input field of the automatic inquiry "QRY-0002", and "automatic close" is stored as the state of inquiry.

In the above description, the answer making unit 7 refers to the inquiry storage unit 10 on the basis of the inquiry ID notified from the determination unit 3, and makes an answer. However, the answer making unit 7 may receive all data necessary to make an answer from the determination unit 3, and make an answer on the basis of the received data. For example, the answer making unit 7 receives an instruction to make an answer to the automatic inquiry "QRY-0002" on the basis of the answer to the automatic inquiry "QRY-0001" from the determination unit 3. Further, the answer making unit 7 receives "systolic blood pressure" which is the modified item, "100" mmHg which is the value before modification, "150" mmHg which is the value after modification, "input error" which is the reason for the modification, and the like with respect to the automatic inquiry "QRY-0001" from the determination unit 3. The answer making unit 7 makes an answer on the basis of these data.

Next, the functional configuration of the terminal 200 will be briefly described. The processing of each functional unit of the terminal 200 is performed by the CPU 201, the ROM 202, and the like in cooperation with each other. Examples of the functional units of the terminal 200 include an input receiving unit and a screen making unit. The input receiving unit receives an input of case data such as a result of diagnostic interview and a result of test from the physician-in-charge or the like via input/output devices such as the keyboard 208 and the mouse 207 provided in the terminal 200. The screen making unit makes, for example, a screen related to an inquiry as shown in FIGS. 14 to 16 described above, and displays the screen on the display 206.

Hereinafter, a flow of the processing performed by the management apparatus according to the example will be described.

FIG. 20 is a flowchart showing an example of the processing performed by the management apparatus according to the example.

Operation S61: When the answer receiving unit 5 receives an answer to one inquiry from the terminal 200, the processing described below will be performed.

Operation S62: The answer receiving unit 5 determines whether or not the case data is modified on the basis of the received answer. If the case data is modified, the process proceeds to S63, and if the case data is not modified, the process ends. Therefore, if the case data is not modified, the logical check is not re-performed.

Operation S63: If the case data is modified, the answer receiving unit 5 instructs the modification unit 6 to modify the case data in the case data storage unit 8. When the modification unit 6 modifies the case data, the modification unit 6 instructs the determination unit 3 to re-perform the logical check on the modified case data. The determination unit 3 re-performs the logical check on the modified case data by referring to the definition table 9.

Operation S64: Next, the determination unit 3 determines whether or not there is another inquiry related to the one inquiry to which an answer including a modification is given. If there is the other inquiry, the process proceeds to Operation S65, and if there is not the other inquiry, the process ends.

Operation S65: The determination unit 3 determines whether or not the other inquiry, which has not been closed or has not been automatically closed, is an automatic inquiry. If the other inquiry is an automatic inquiry, the process proceeds to S66, and if other inquiry is a manual inquiry, the process returns to S64. Therefore, if the other inquiry is a manual inquiry, the answer is not made and the inquiry is not automatically closed.

Operation S66: The determination unit 3 determines whether or not the cause of the other inquiry is solved by re-performing the logical check. If the cause of the inquiry is solved, the process proceeds to S67, and if the cause of the inquiry is not solved, the process proceeds to S69.

Operation S67: Since the cause of the other inquiry is solved, the determination unit 3 issues an answer making instruction to the answer making unit 7. The answer making unit 7 makes an answer to the other automatic inquiry on the basis of the answer making instruction.

Operation S68: When the answer making unit 7 makes an answer to the other automatic inquiry, the answer making unit 7 automatically closes the other automatic inquiry. The process returns to S64 to determine whether or not there is further another inquiry.

Operation S69: If the cause of the other automatic inquiry is not solved, the inquiry storage unit 10 holds the other automatic inquiry without change.

A computer program that causes a computer to perform the above-described method and a computer-readable non-transitory storage medium that records the program are included in the scope of the present invention. Here, examples of the computer-readable non-transitory storage medium include a flexible disk, a hard disk, CD-ROM (Compact Disc-Read Only Memory), MO (Magneto Optical disk), DVD, DVD-ROM, DVD-RAM (DVD-Random Access Memory), BD (Blue-ray Disc), a USB memory, and a semiconductor memory. The computer program is not limited to a program recorded on the above-described recording media, but the computer program may be transmitted via a telecommunication line, a wireless or wired communication line, a network typified by the Internet, and the like.

(a) Modified Example 1

In the embodiment and the example described above, although the one inquiry to which a user makes an answer is an automatic inquiry, the one inquiry may be a manual inquiry.

Specifically, in the embodiment and the example described above, if an answer to the one automatic inquiry by a user solves a cause of another automatic inquiry, the management apparatus 100 makes an answer to the other automatic inquiry on the basis of the answer to the one automatic inquiry. Thereafter, the management apparatus 100 closes the other automatic inquiry. For example, in Operation S12 to Operation S14 of FIG. 3, when the cause of the automatic inquiry (A2) is solved (Operation S12), the management apparatus 100 makes an answer to the automatic inquiry (A2) (Operation S13) and automatically closes the automatic inquiry (A2).

However the one inquiry may be a manual inquiry. For example, if an answer to one manual inquiry solves a cause of another automatic inquiry, the management apparatus 100 makes an answer to the other automatic inquiry on the basis of the answer to the one manual inquiry.

In the embodiment and the example described above, although an inquiry to which the management apparatus 100 makes an answer is an automatic inquiry, the inquiry may be a manual inquiry. For example, if an answer to one automatic inquiry solves a cause of another manual inquiry, the management apparatus 100 makes an answer to the other manual inquiry on the basis of the answer to the one automatic inquiry.

In the embodiment and the example described above, although an automatic close is set to an automatic inquiry, an automatic close is set to a manual inquiry. For example, if an answer to one automatic inquiry solves a cause of another manual inquiry, the management apparatus 100 makes an answer to the other manual inquiry, and automatically closes the other manual inquiry.

In the embodiment and the example described above, although the management apparatus 100 automatically closes an automatic inquiry whose cause is solved, the management apparatus 100 does not necessarily has to automatically close the automatic inquiry, but may hold the automatic inquiry without change. For example, if an answer to one inquiry solves a cause of another automatic inquiry, the management apparatus 100 makes an answer to the other automatic inquiry, and holds the other automatic inquiry without change.

A summary of the modified example described above is as follows.

One inquiry to which a user makes an answer may be either an automatic inquiry or a manual inquiry.

An inquiry to which the management apparatus 100 makes an answer may be either an automatic inquiry or a manual inquiry.

If a cause of an automatic inquiry or a manual inquiry is solved by an answer made by a user, the automatic inquiry or the manual inquiry is automatically closed or held without change.

On the basis of these conditions described above, first, the management apparatus 100 receives an answer to one automatic inquiry or one manual inquiry made by a user. Next, the management apparatus 100 determines whether or not a cause of another automatic inquiry or another manual inquiry is solved by the answer. If the cause is solved, the management apparatus 100 makes an answer to the other automatic inquiry or the other manual inquiry on the basis of the answer to the one automatic inquiry or the one manual inquiry. Thereafter, the management apparatus 100 automatically closes the other automatic inquiry or the other manual inquiry, or holds the other automatic inquiry or the other manual inquiry without change.

(b) Modified Example 2

In the embodiment and the example described above, the case in which a cause of another inquiry is solved is a case in which an answer to one inquiry includes a modification of case data and the cause of the inquiry is solved due to the modification. In addition, examples of the case in which a cause of another inquiry is solved include a case in which an error of an item field where case data should be inputted becomes clear by an answer to one inquiry and the other inquiry itself disappears.

For example, it is assumed that both one inquiry and the other inquiry are inquires about an item A. Here, a case in which an answer to the one inquiry reveals that data which should be inputted into an item B is inputted into the item A corresponds to the case of this modified example.

For example, the answer receiving unit 5 receives a change of item field into which case data is inputted, case data in the changed item field, a deletion of case data in an item field before change, and the like as an answer to the one inquiry on another answer screen. At this time, when the input position of the case data is changed from the item A to the item B by the answer to the one inquiry, the cause of the other inquiry about the item A is solved.

A specific example will be described below. It is assumed that "5000" mmHg is inputted as case data of the systolic blood pressure with respect to a certain human subject ID and a certain date of diagnostic interview. The diastolic blood pressure is assumed to be "100" mmHg. The determination unit 3 performs the logical check on the systolic blood pressure "5000" mmHg by referring to the definition table 9 shown in FIG. 12. Here, the systolic blood pressure "5000" mmHg satisfies the first criterion that the data type is "numerical value". However, the systolic blood pressure "5000" mmHg does not satisfy the second criterion that the maximum number of digits is "3", the third criterion that the allowed value range is "110 to 180" mmHg, and the fourth criterion that the relationship between items is "systolic blood pressure>diastolic blood pressure". Therefore, the inquiry making unit 4 determines that the systolic blood pressure "5000" mmHg does not satisfy the second criterion, the third criterion, and the fourth criterion, and makes an automatic inquiry (second criterion), an automatic inquiry (third criterion), and an automatic inquiry (fourth criterion).

Next, the answer receiving unit 5 receives "the number of white blood cells" as the item field after change, "5000" as the case data after change, and "systolic blood pressure" as the item field to be deleted as an answer to the automatic inquiry (second criterion). The modification unit 6 modifies the case data on the basis of the answer. The determination unit 3 re-performs the logical check on the basis of the answer to the automatic inquiry (second criterion). Here, the case data of the "systolic blood pressure" is deleted, so that the causes of the automatic inquiry (third criterion) and the automatic inquiry (fourth criterion) related to the "systolic blood pressure" are solved. As a result, the causes of the automatic inquiry (third criterion) and the automatic inquiry (fourth criterion) are solved on the basis of the answer to the automatic inquiry (second criterion). Based on the information described above, the determination unit 3 instructs the answer making unit 7 to make answers to the automatic inquiry (third criterion) and the automatic inquiry (fourth criterion).

Next, when the answer making unit 7 determines that an item field is changed, for example, selects a phrase of a phrase ID "K0002" which has a keyword of "error of item field". Then, the answer making unit 7 makes answers to the automatic inquiry (third criterion) and the automatic inquiry (fourth criterion) on the basis of the phrase.

(c) Modified Example 3

In the embodiment and the example described above, an example in which the management system 1000 includes only the management apparatus 100 and the terminal 200 is described. However, the management system 1000 may further includes a test facility terminal 300 and a pharmaceutical company terminal 400.

FIG. 21 is an example of a network configuration diagram according to another management system. The management system 1000 in FIG. 21 includes the management apparatus 100, the terminal 200 installed in a medical facility, the test facility terminal 300 installed in a test facility, and a pharmaceutical company terminal 400 installed in a pharmaceutical company. The management apparatus 100 is connected with the terminal 200, the test facility terminal 300, and the pharmaceutical company terminal 400 via networks 50, 51, and 52 respectively. A terminal or a user allowed to access the management apparatus 100 can access the case data managed by the management apparatus 100 via each terminal. For example, a person in charge in the pharmaceutical company can refer to content of the case data from the pharmaceutical company terminal 400 installed in the pharmaceutical company.

In such a management system 1000, an answer to an automatic inquiry and a manual inquiry issued from the management apparatus 100 can be inputted from the terminal 200, the test facility terminal 300, or the pharmaceutical company terminal 400. Therefore, when an answer to one inquiry is inputted from any one of the terminals 200, 300, and 400, the management apparatus 100 can make an answer to another inquiry in the same manner as in the embodiment and the example described above.

(d) Modified Example 4

Although, in the embodiment and the example described above, a clinical trial of new drug is used as an example, the present invention is not limited to this. For example, the present invention can be applied to any test including a clinical trial of food, cosmetics, and a generic drug, and a clinical trial to check the efficacy and effect of a medical device.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory storage medium storing a management program, the management program causing a computer to execute:
    first receiving case data related to a result of a clinical trial;
    referring to a definition table storing a first criterion and a second criterion;
    first determining whether or not the case data satisfies the first criterion stored in the definition table;
    first transmitting a first inquiry to a terminal when the case data does not satisfy the first criterion;
    second determining whether or not the case data satisfies the second criterion stored in the definition table;
    second transmitting a second inquiry to the terminal when the case data does not satisfy the second criterion;
    second receiving a first answer to the first inquiry from the terminal, the first answer including other case data that is the case data at least a part of which is modified;
    third determining whether or not the other case data satisfies the second criterion; and
    making a second answer to the second inquiry when the other case data satisfies the second criterion; and
    changing a state of the second inquiry transmitted to the terminal, from an issued state to a closed state, when the other case data satisfies the second criterion.

2. The non-transitory storage medium storing the management program according to claim 1, causing the computer to further execute:
    referring to the definition table in which some of a plurality of criteria including the first criterion and the second criterion are associated with each of a plurality of items into which the case data is classified;
    fourth determining whether or not the first criterion and the second criterion are conditions related to the same item in the plurality of items; and
    the third determining determines whether or not the other case data satisfies the second criterion when the first criterion and the second criterion are conditions related to the same item.

3. The non-transitory storage medium storing the management program according to claim 1, causing the computer to further execute:
    storing the second inquiry and the first answer in association with each other into an inquiry storage unit when the second answer, which includes information indicating that the second answer is made on the basis of the first answer, is made.

4. The non-transitory storage medium storing the management program according to claim 1, causing the computer to further execute:
    storing the second inquiry and the first answer in association with each other into an inquiry storage unit when the second answer, which includes the case data and the other case data, is made.

5. The non-transitory storage medium storing the management program according to claim 1, causing the computer to further execute:
    deleting the second inquiry from an inquiry list which is displayed on a display screen of the terminal when the other case data is determined to satisfy the second criterion.

6. The non-transitory storage medium storing the management program according to claim 1, causing the computer to further execute:
    when receiving the first answer, in which case data corresponding to a first item among a plurality of items into which the case data is classified is modified to the other case data corresponding to a second item different from the first item, to the first inquiry,
    referring to the definition table by associating some of a plurality of criteria including the first criterion and the second criterion with each of the plurality of items, and determining whether or not the other case data satisfies a third criterion corresponding to the second item.

7. A management apparatus comprising:
- a receiving unit configured to receive case data related to a result of a clinical trial;
- a definition table to store a first criterion and a second criterion;
- a determination unit configured to determine whether or not the case data that is received satisfies the first criterion stored in the definition table, and to determine whether or not the case data satisfies the second criterion stored in the definition table;
- an inquiry making unit configured to transmit a first inquiry to a terminal when the case data does not satisfy the first criterion and to transmit a second inquiry to the terminal when the case data does not satisfy the second criterion;
- an answer receiving unit configured to receive a first answer to the first inquiry from the terminal, the first answer including other case data that is the case data at least a part of which is modified; and
- an answer making unit configured to make a second answer to the second inquiry when the other case data satisfies the second criterion and to change a state of the second inquiry transmitted to the terminal, from an issued state to a closed state, when the other case data satisfies the second criterion.

8. The management apparatus according to claim 7, wherein
- the definition table further stores some of a plurality of criteria including the first criterion and the second criterion in association with each of a plurality of items into which the case data is classified,
- the determination unit determines whether or not the first criterion and the second criterion are conditions related to the same item in the plurality of items and determines whether or not the other case data satisfies the second criterion when the first criterion and the second criterion are conditions related to the same item, and
- the answer making unit makes the second answer on the basis of a result of the determination.

9. The management apparatus according to claim 7, wherein
- the answer making unit makes the second answer including information indicating that the second answer is made on the basis of the first answer and stores the second inquiry and the first answer in association with each other into an inquiry storage unit.

10. The management apparatus according to claim 7, wherein
- the answer making unit makes the second answer including the case data and the other case data and stores the second inquiry and the first answer in association with each other into an inquiry storage unit.

11. The management apparatus according to claim 7, wherein
- the answer making unit deletes the second inquiry from an inquiry list which is displayed on a display screen of the terminal when the other case data is determined to satisfy the second criterion.

12. The management apparatus according to claim 7, wherein
- when the answer receiving unit receives the first answer, in which case data corresponding to a first item among a plurality of items into which the case data is classified is modified to the other case data corresponding to a second item different from the first item, to the first inquiry, the determination unit refers to the definition table by associating some of a plurality of criteria including the first criterion and the second criterion with each of the plurality of items, and determines whether or not the other case data satisfies a third criterion corresponding to the second item.

13. A management method executed by a computer comprising:
- first receiving case data related to a result of a clinical trial;
- referring to a definition table storing a first criterion and a second criterion;
- first determining whether or not the case data satisfies the first criterion stored in the definition table;
- first transmitting a first inquiry to a terminal when the case data does not satisfy the first criterion;
- second determining whether or not the case data satisfies the second criterion stored in the definition table;
- second transmitting a second inquiry to the terminal when the case data does not satisfy the second criterion;
- second receiving a first answer to the first inquiry from the terminal, the first answer including other case data that is the case data at least a part of which is modified;
- third determining whether or not the other case data satisfies the second criterion; and
- making a second answer to the second inquiry when the other case data satisfies the second criterion; and
- changing a state of the second inquiry transmitted to the terminal, from an issued state to a closed state, when the other case data satisfies the second criterion.

14. The management method according to claim 13, further comprising:
- referring to the definition table in which some of a plurality of criteria including the first criterion and the second criterion are associated with each of a plurality of items into which the case data is classified;
- fourth determining whether or not the first criterion and the second criterion are conditions related to the same item in the plurality of items; and
- the third determining determines whether or not the other case data satisfies the second criterion when the first criterion and the second criterion are conditions related to the same item.

15. The management method according to claim 13, further comprising:
- storing the second inquiry and the first answer in association with each other into an inquiry storage unit when the second answer, which includes information indicating that the second answer is made on the basis of the first answer, is made.

16. The management method according to claim 13, further comprising:
- storing the second inquiry and the first answer in association with each other into an inquiry storage unit when the second answer, which includes the case data and the other case data, is made.

17. The management method according to claim 13, further comprising:
- deleting the second inquiry from an inquiry list which is displayed on a display screen of the terminal when the other case data is determined to satisfy the second criterion.

18. The management method according to claim 13, further comprising:
- when receiving the first answer, in which case data corresponding to a first item among a plurality of items into which the case data is classified is modified to the other case data corresponding to a second item different from the first item, to the first inquiry,
- referring to the definition table by associating some of a plurality of criteria including the first criterion and the second criterion with each of the plurality of items, and determining whether or not the other case data satisfies a third criterion corresponding to the second item.

19. A management apparatus comprising:
a memory which stores a program; and
a processor which executes, based on the program, a procedure comprising:
receiving case data related to a result of a clinical trial;
determining whether the case data that is received satisfies a first criterion included in a definition information, and to determining whether the case data satisfies a second criterion included in the definition information;
transmitting a first inquiry to a terminal when the case data does not satisfy the first criterion and transmitting a second inquiry to the terminal when the case data does not satisfy the second criterion;
receiving a first answer to the first inquiry from the terminal, the first answer including other case data that is the case data at least a part of which is modified; and
making a second answer to the second inquiry when the other case data satisfies the second criterion and to change a state of the second inquiry transmitted to the terminal, from an issued state to a closed state, when the other case data satisfies the second criterion.

20. The management apparatus according to claim 19, wherein
the definition information includes some of a plurality of criteria including the first criterion and the second criterion in association with each of a plurality of items into which the case data is classified,
wherein the procedure comprises:
executing a determination whether the first criterion and the second criterion are conditions related to the same item in the plurality of items and whether the other case data satisfies the second criterion when the first criterion and the second criterion are conditions related to the same item; and making the second answer on the basis of a result of the determination.

21. The management apparatus according to claim 19, wherein the procedure comprises:
making the second answer including information indicating that the second answer is made on the basis of the first answer and storing the second inquiry and the first answer in association with each other into an inquiry storage.

22. The management apparatus according to claim 19, wherein the procedure comprises:
making the second answer including the case data and the other case data and storing the second inquiry and the first answer in association with each other into an inquiry storage.

23. The management apparatus according to claim 19, wherein the procedure comprises:
deleting the second inquiry from an inquiry list which is displayed on a display screen of the terminal when the other case data is determined to satisfy the second criterion.

24. The management apparatus according to claim 19, wherein the procedure comprises:
when the first answer, in which case data corresponding to a first item among a plurality of items into which the case data is classified is modified to the other case data corresponding to a second item different from the first item, is received,
referring to the definition information by associating some of a plurality of criteria including the first criterion and the second criterion with each of the plurality of items, and determining whether the other case data satisfies a third criterion corresponding to the second item.

* * * * *